United States Patent [19]
Yuyama et al.

[11] Patent Number: 5,671,592
[45] Date of Patent: Sep. 30, 1997

[54] MEDICINE PACKING APPARATUS

[75] Inventors: Shoji Yuyama, Toyonaka; Takaaki Murakami, Osaka; Kunihiko Kano, Toyonaka, all of Japan

[73] Assignee: Yuyama Mfg. Co., Ltd., Osaka-fu, Japan

[21] Appl. No.: 522,491

[22] Filed: Aug. 31, 1995

[30] Foreign Application Priority Data

Oct. 21, 1994 [JP] Japan ..................... 6-256542

[51] Int. Cl.⁶ .................. B65B 1/04; B65B 1/30
[52] U.S. Cl. .................. 53/493; 53/55; 53/168
[58] Field of Search ............. 53/493, 495, 168, 53/55, 52, 507, 508, 77; 221/2, 129, 197, 123, 71

[56] References Cited

U.S. PATENT DOCUMENTS

| | | | |
|---|---|---|---|
| 3,871,156 | 3/1975 | Koenig et al. | 53/168 X |
| 4,655,026 | 4/1987 | Wigoda | 53/55 |
| 4,664,289 | 5/1987 | Shimizu et al. | 221/2 |
| 4,870,799 | 10/1989 | Bergerioux et al. | 53/55 |
| 4,903,861 | 2/1990 | Yuyama | 221/265 |
| 5,010,929 | 4/1991 | Tisma | 53/168 X |
| 5,097,652 | 3/1992 | Inamura et al. | 53/168 X |
| 5,502,944 | 4/1996 | Kraft et al. | 53/55 |

FOREIGN PATENT DOCUMENTS

| | | |
|---|---|---|
| 58-99963 | 6/1983 | Japan . |
| 60-21761 | 2/1985 | Japan . |
| 3-41208 | 6/1991 | Japan . |
| 3-58743 | 9/1991 | Japan . |
| 5-47441 | 7/1993 | Japan . |

*Primary Examiner*—James F. Coan
*Attorney, Agent, or Firm*—Wenderoth, Lind & Ponack

[57] ABSTRACT

A medicine packing apparatus includes medicine storage shelves for storing a large number of medicine containers having medicines contained therein, and a comparatively small number of medicine feeders on each of which one of the large number of medicine containers is set for feeding medicine in a quantity conforming to a prescription. Store location memory means and set location memory means are provided which respectively memorize data on the store location of each individual medicine in the storage shelves and data on set location of the medicine in the feeders. If a medicine container corresponding to a prescription is not present in the set location, a search is made in the storage shelves, and then the searched location of the medicine is indicated accordingly. When a medicine container taken out from the storage shelves is set on one of the feeders, an identification device provided on the medicine container is read by a reader, and data on the set location is stored into a set location memory.

19 Claims, 19 Drawing Sheets

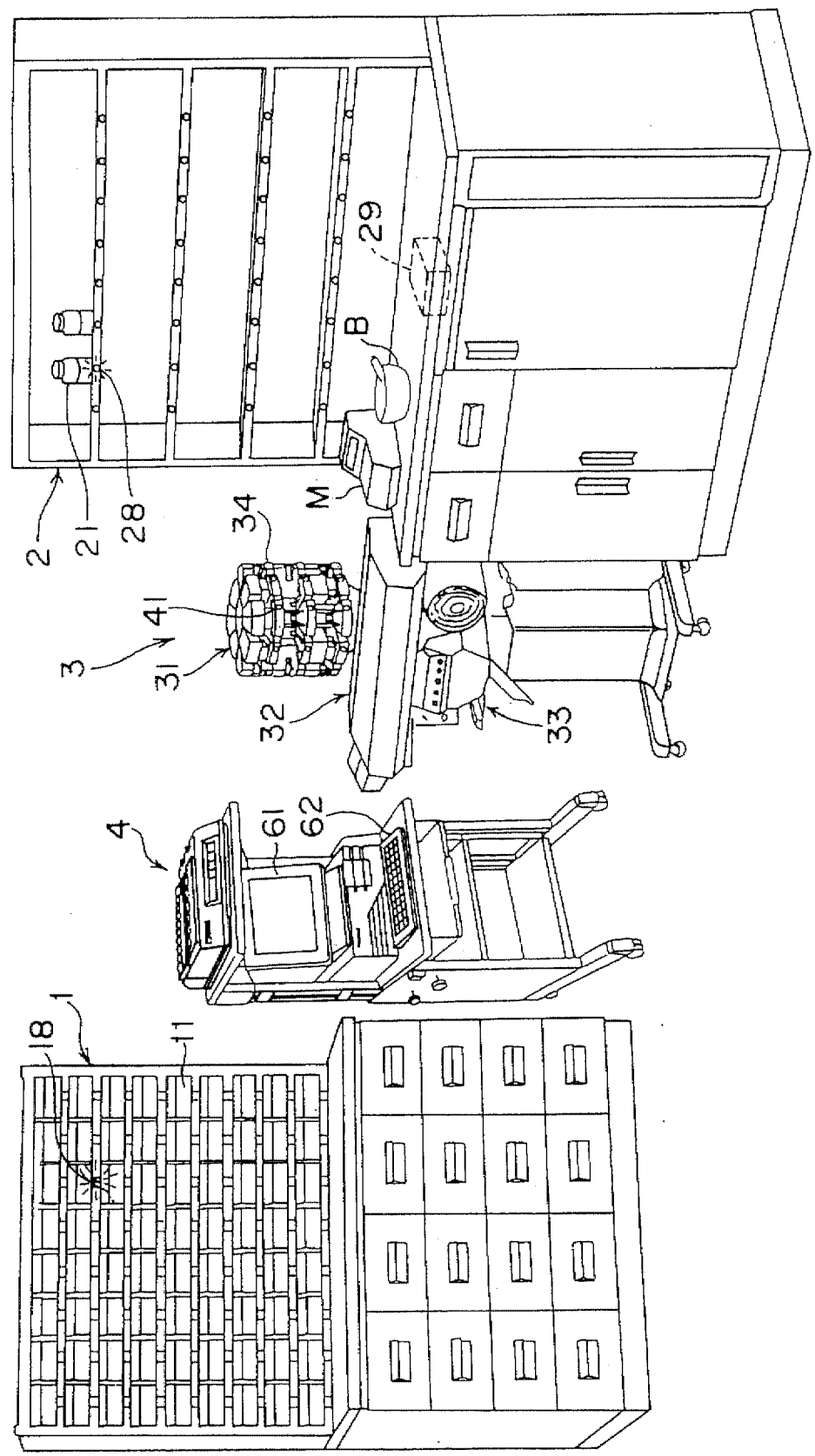

MEDICINE PACKING APPARATUS

BACKGROUND OF THE INVENTION

The present invention relates generally to a medicine packing apparatus, more particularly, to a medicine packing apparatus in which a medicine container corresponding to a prescription is taken out from medicine storage shelves to set on a medicine feeder means, and which enables the medicine container to be readily searched and identified.

Medicine packing apparatus has been known hitherto in which a plurality of medicine cartridges each housing a medicine in the form of tablet or the like are individually set in medicine feeders so that medicines are selectively fed from the individual feeders for being automatically packed by one dose.

Medicine packing apparatus of this type is very large in size because the apparatus includes a large number of medicine feeders arranged in a cylindrical fashion or in a drawer pattern. Therefore, the apparatus is too large to be placed in a dispensary of a small-scale hospital and/or in a pharmacy and, moreover, it involves some difficulty in the insertion and extraction of medicine cartridges.

Each medicine cartridge is previously specified for placement in a particular medicine feeder. Therefore, when plural medicine cartridges are removed for medicine replenishment, for example, it is possible that they may be set in wrong medicine feeders, with the result that medicines different from those of a prescription may be packed.

Further, in a conventional medicine packing apparatus, the name of the medicine to be fed from each respective medicine feeder is previously recorded. This requires that each time the medicine cartridge set in a medicine feeder is replaced by one for a different medicine, data for medicine name should be input anew, which is rather troublesome.

SUMMARY OF THE INVENTION

The present invention has been developed in view of the above-identified problems with the prior art.

It is an object of the invention to provide a compact and easy-to-handle medicine packing apparatus which includes medicine storage shelves for storing a large number of medicine containers (medicine cartridges) and a relatively small number of medicine feed means (medicine feeders) such that one medicine feed means is commonly used for a multiplicity of medicine containers, whereby only necessary medicine containers may be taken out from the shelves and set in a medicine feed means.

It is another object of the invention to provide a medicine packing apparatus which makes it possible to readily and quickly search and take out any medicine container corresponding to a prescription from among many medicine containers stored in the medicine storage shelves.

It is a further object of the invention to provide a medicine packing apparatus of such arrangement that when a medicine container is stored at any location in the medicine storage shelves, the medicine container is immediately identified so that it can be easily located later.

It is another object of the invention to provide a medicine packing apparatus including identification means such that if any medicine container is set in a wrong position or if the container is replaced by another medicine container, the location at which the container is placed is immediately identified so that any incorrect packing can be prevented.

It is still another object of the invention to provide a medicine delivery apparatus having features similar to those of the above mentioned medicine packing apparatus.

(1) In order to accomplish the foregoing objects, in a first aspect of the present invention, there is provided a medicine packing apparatus, applicable primarily to tablet packing, which comprises:

medicine storage shelves for storing a large number of medicine containers each having a medicine contained therein;

a relatively small number of medicine feed means on each of which one of the medicine containers is set for feeding a medicine in a quantity conforming to a prescription;

packing means for packing the medicine fed from the medicine feed means by one dose;

identification means provided for each of the medicine containers;

read means for reading medicine data from the identification means of the medicine container set on the medicine feed means;

set location memory means for memorizing the set location for the medicine container on the basis of the medicine data read by the read means; and set location search means for searching, on the basis of the set location data for each medicine memorized in the set location memory means, the medicine feed means on which a medicine container for the medicine corresponding to the prescription is set.

In the apparatus according to the first mentioned arrangement, a medicine container corresponding to a prescription is taken out from the medicine storage shelves and is set on the medicine feed means. Then, the medicine data is read by the read means from the identification means of the medicine container, so that the set location for the medicine is memorized into the set location memory means. On the basis of set location data for each individual medicine memorized in the set location memory means, the medicine feed means on which the medicine container corresponding to the prescription is set is searched by the set location search means. Packing of the medicine is performed by the searched medicine feed means and the packing means in combination.

According to the first aspect of the invention, a comparatively small number of medicine containers are to be set in position, while a majority of the remaining containers are intensively stored in the medicine storage shelves. This provides for size reduction of the apparatus, and enables easy setting and convenient use at a pharmacy or dispensary in a small hospital. It is only required that medicine containers corresponding to a prescription may be taken out from the storage shelves and set on any available medicine feed means, or set in replacement for medicine containers earlier set in position. This affords ease of handling.

(2) In a second aspect of the invention, there is provided a medicine packing apparatus, applicable primarily to powder packing, which comprises:

medicine storage shelves for storing a large number of medicine containers each having a medicine contained therein;

a relatively small number of medicine feed means on each of which one of the medicine containers is set for feeding a medicine in a quantity conforming to a prescription;

medicine distributing means for annularly uniformly distributing the medicine fed from the medicine feed means over a distributing board and then dividing the medicine by one dose to discharge the same;

packing means for packing the medicine discharged from the medicine distributing means by one dose;

identification means provided for each of the medicine containers;

read means for reading medicine data from the identification means of the medicine container set on the medicine feed means;

set location memory means for memorizing the set location for the medicine container on the basis of the medicine data read by the read means; and set location search means for searching, on the basis of the set location data for each medicine memorized in the set location memory means, the medicine feed means on which a medicine container for the medicine corresponding to the prescription is set.

In the apparatus according to the second mentioned arrangement, a medicine feed means on which a medicine container corresponding to the prescription is set is searched by the set location search means in the same manner as the first aspect of the invention. Then, packing of the medicine is performed by the searched medicine feed means, medicine distributing means, and packing means in combination.

The invention, in its second aspect, demonstrates effects similar to those according to the first aspect.

(3) In a third aspect of the invention, the medicine packing apparatus according to the first or second aspect, further comprises:

store location memory means for memorizing a store location fixed for each medicine container in the medicine storage shelves;

store location search means for searching the store location for the medicine corresponding to the prescription on the basis of the store location data memorized in the store location memory means; and store location indicator means for indicating the store location for the medicine searched by the store location search means.

In the apparatus according to the third mentioned arrangement, if the medicine container corresponding to the prescription is not set on any medicine feed means, the store location of the medicine container is searched by the store location search means, and the store location is indicated by the store location indicator means. Thus, when a medicine container is taken out from the particular shelf indicated, the medicine is what is corresponding to the prescription.

According to the third aspect of the invention, store location of any medicine container corresponding to the prescription is indicated, which eliminates the trouble of search and permits easy and quick removal of the container from the storage.

(4) In a fourth aspect of the invention, the medicine packing apparatus according to the first or second aspect, further comprises:

read means for reading medicine data from the identification means of the medicine container stored in each store location of the medicine storage shelves;

store location memory means for memorizing a store location for each medicine container on the basis of medicine data read by the read means;

store location search means for searching the store location for the medicine corresponding to the prescription on the basis of the store location data memorized in the store location memory means; and store location indicator means for indicating the store location for the medicine searched by the store location search means.

In the apparatus according to the fourth mentioned arrangement, whenever a medicine container is stored at any location in the medicine storage shelves, the relevant medicine data is read by the identification means of the medicine container so that the data on the store location is stored into the store location memory means. Therefore, when a medicine container is taken out from the particular shelf indicated by the store location indicator means, the medicine container is what is corresponding to the prescription.

According to the fourth aspect of the invention, each medicine container may be stored at any free location. When taking out a medicine container, it is only required that the one at an indicated location may be taken out. This eliminates possible limitation on store location, saves the trouble of locating, and permits easy and quick removal from storage.

(5) In a fifth aspect of the invention, the medicine packing apparatus according to one of the first to fourth aspects further comprises:

proper set location memory means for memorizing a proper set location fixed for each medicine container in the medicine feed means;

proper location search means for searching the proper set location for the medicine corresponding to the prescription on the basis of the proper location data memorized in the proper set location memory means; and proper set location indicator means for indicating the proper set location for the medicine searched by the proper location search means.

In the apparatus according to the fifth mentioned arrangement, a medicine container corresponding to the prescription is taken out from the shelf and is set in place as indicated by the set location indicator means. In that case, if the location is already occupied by another medicine container, the prior occupant is removed for replacement.

According to the fifth aspect of the invention, it is only required that any medicine container may be set at an indicated location, which involves no doubt as to the location for setting. This permits quick and easy setting.

(6) In a sixth aspect of the invention, the medicine packing apparatus according to the fifth aspect is further characterized in that the proper set location memory means memorize the proper set location fixed for each medicine container in such a condition that the medicine which is likely to bounce when dropped is set at a lower location, and that the medicine which is less likely to bounce when dropped is set at a higher location.

In the apparatus according to the sixth mentioned arrangement, packing is carried out at constant speed irrespective of whether the medicine is likely to bounce or less likely to bounce.

According to the sixth aspect of the invention, a set location compatible with the attribute of the medicine, i.e., bouncing behavior, is indicated. Setting at the indicated location permits smooth packing at constant speed.

(7) In a seventh aspect of the invention, the medicine packing apparatus according to one of the first to fourth aspects is further characterized in that the packing means performs packing of the medicine corresponding to the prescription at a packing velocity set in consideration of the set location for the medicine and attributes of the medicine including bouncing and rolling characteristics.

In the apparatus according to the seventh mentioned arrangement, the velocity of packing is adjusted according to the attributes of the tablet set in position and the height of the set Location.

This permits smooth packaging even if the cartridge is set at any location.

(8) In an eighth aspect of the invention, there is provided a medicine packing apparatus, applicable mainly to powder packing, which comprises:

medicine storage shelves for storing a large number of medicine containers each having a medicine contained therein;

a plurality of hoppers for receiving a medicine dispensed according to a prescription;

medicine distributing means for annularly uniformly distributing the medicine fed from the hoppers on a distributing board and then dividing the medicine by one dose to discharge the same;

packing means for packing the medicine discharged from the medicine distributing means by one dose;

identification means provided for each of the medicine containers;

read means for reading medicine data from the identification means; and medicine check means for checking the medicine by comparing the medicine data read by the read means with the prescription data.

In the apparatus according to the eighth mentioned arrangement, the medicine data for a medicine container taken out from the medicine storage shelves is read by the read means and checked by the medicine check means. Medicines, taken out from individual medicine containers so checked, are dispensed and introduced into one of the hoppers. The medicines are then divided by one dose by the medicine distributing means and are packed one by one by the packing means.

According to the eighth aspect of the invention, data is checked with respect to each medicine container taken out from the medicine storage shelves. This insures that there is no possibility of any medicine being taken out which is different from the prescription, which results in improved safety.

(9) In a ninth aspect of the invention, the medicine packing apparatus according to the eighth aspect further comprises:

store location memory means for memorizing a store location fixed for each medicine container in the medicine storage shelves;

store location search means for searching the store location for the medicine corresponding to the prescription on the basis of the store location data memorized in the store location memory means; and store location indicator means for indicating the store location for the medicine searched by the store location search means.

In the apparatus according to the ninth mentioned arrangement, the store location for a medicine container corresponding to the prescription is indicated by the store location indicator means. Thus, when a medicine container is taken out from the particular shelf indicated by the indicator means, the medicine is what is corresponding to the prescription.

The invention, in its ninth aspect, demonstrates effects similar to those according to the third and fourth aspects.

(10) In a tenth aspect of the invention, the medicine packing apparatus according to the eighth aspect further comprises:

read means for reading medicine data from the identification means of the medicine container stored in each store location of the medicine storage shelves;

store location memory means for memorizing a store location for each medicine container on the basis of medicine data read by the read means;

store location search means for searching the store location for the medicine corresponding to the prescription on the basis of the store location data memorized in the store location memory means; and store location indicator means for indicating the store location for the medicine searched by the store location search means.

In the apparatus according to the tenth mentioned arrangement, whenever a medicine container is stored at any location in the medicine storage shelves, the relevant medicine data is read by the identification means of the medicine container so that the data on the store location is stored into the store location memory means. Therefore, when a medicine container is taken out from the particular shelf indicated by the store location indicator means, the medicine container is what is corresponding to the prescription.

The invention, in its tenth aspect, demonstrates effects similar to those according to the third and fourth aspects.

(11) According to an eleventh aspect of the invention, there is provided a medicine packing apparatus, applicable mainly to ampule delivering, which comprises:

medicine storage shelves for storing a large number of medicine containers each having a medicine contained therein;

a relatively small number of medicine delivery means on each of which one of the medicine containers is set for delivering a medicine in a quantity conforming to a prescription;

identification means provided in for each of the medicine containers;

read means for reading medicine data from the identification means of the medicine container set on the medicine delivery means;

set location memory means for memorizing the set location for the medicine container on the basis of the medicine data read by the read means; and set location search means for searching, on the basis of the set location data for each medicine memorized in the set location memory means, the medicine delivery means on which a medicine container for the medicine corresponding to the prescription is set.

In the apparatus according to the eleventh mentioned arrangement, a medicine container corresponding to a prescription is taken out from the medicine storage shelves and set on the medicine delivery means. Then, the medicine data is read by the read means from the identification means of the medicine container, whereupon the set location for the medicine is memorized into the set location memory means. On the basis of the set location data for each individual medicine memorized in the set location memory means, the medicine delivery means corresponding to the prescription is searched by the control means. Delivery of the medicine is performed by the medicine delivery means.

The invention, in its eleventh aspect, demonstrates effects similar to those according to the first, second and third aspects.

(12) In a twelfth aspect of the invention, the medicine packing apparatus according to the eleventh aspect further comprises:

store location memory means for memorizing a store location fixed for each medicine container in the medicine storage shelves;

store location search means for searching the store location for the medicine corresponding to the prescription on the basis of the store location data memorized in the store location memory means; and store location indicator means for indicating the store location for the medicine searched by the store location search means.

In the apparatus according to the twelfth mentioned arrangement, if the medicine container corresponding to the prescription is not set on any medicine delivery means, the store location of the medicine container is indicated by the store location indicator means. Therefore, when a medicine container is taken out from the particular shelf indicated, the medicine is what is corresponding to the prescription.

The invention, in its twelfth aspect, demonstrates effects similar to those according to the first, second and third aspects.

(13) In a thirteenth aspect of the invention, the medicine packing apparatus according to the twelfth aspect further comprises:

read means for reading medicine data from the identification means of the medicine container stored in each store location of the medicine storage shelves;

store location memory means for memorizing the store location for each medicine container on the basis of medicine data read by the read means;

store location search means for searching the store location for the medicine corresponding to the prescription on the basis of the store location data memorizing in the store location memory means; and store location indicator means for indicating the store location for the medicine searched by the store location search means.

In the apparatus according to the thirteenth mentioned arrangement, whenever a medicine container is stored at any location in the medicine storage shelves, the relevant medicine data is read by the identification means of the medicine container so that the data on the store location is stored into the store location memory means. Therefore, when a medicine container is taken out from the particular shelf indicated by the store location indicator means, the medicine container is what is corresponding to the prescription.

The invention, in its thirteenth aspect, demonstrates effects similar to those according to the first, second and third aspects.

BRIEF DESCRIPTION OF THE DRAWINGS

Further objects and advantages of the present invention will become clear from the following description taken in conjunction with the preferred embodiments thereof with reference to the accompanying drawings, in which:

FIG. 1 is a general view in perspective showing a first embodiment of the medicine packing apparatus in accordance with the present invention;

Figure 2A:
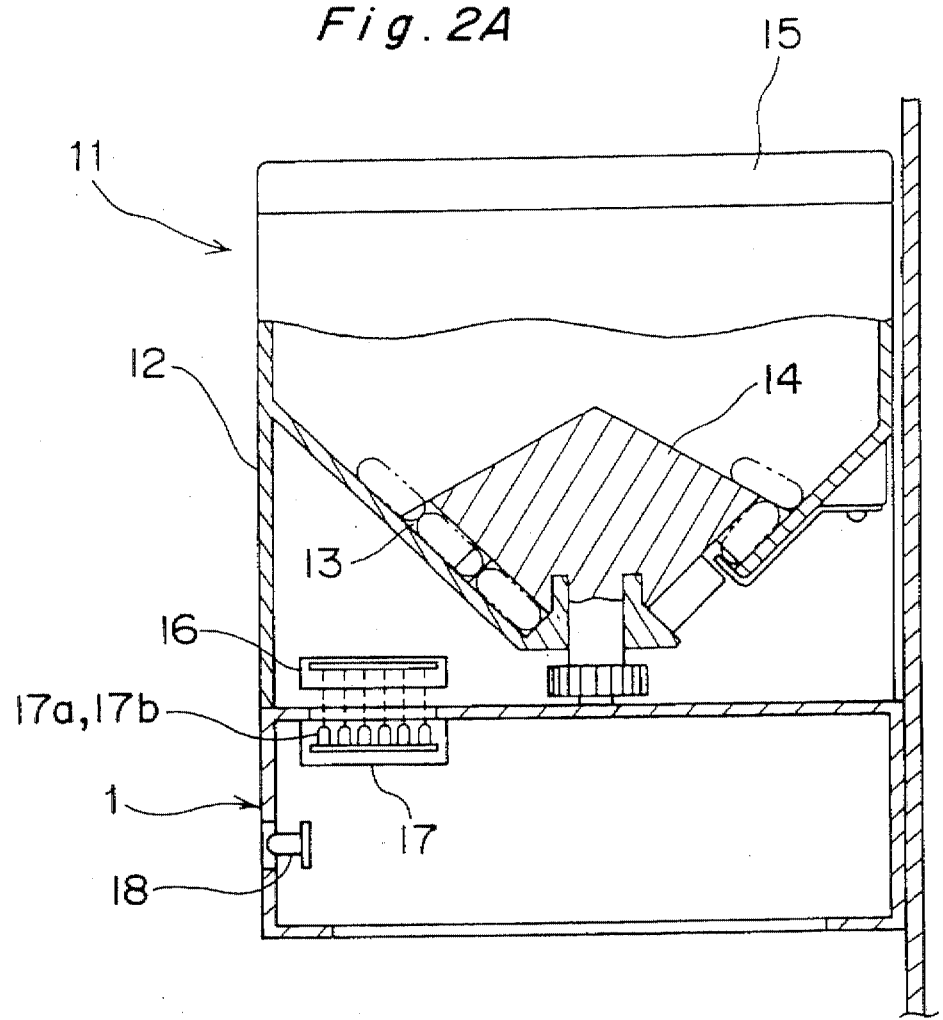
FIG. 2A is a sectional view showing a tablet cartridge and a tablet storage shelf.

DETAILED DESCRIPTION OF THE PREFERRED EMBODIMENTS (1) First Embodiment

FIG. 1 illustrates a general arrangement of a medicine packing apparatus according to the invention. The apparatus can be employed in packing both tablets and powder. In the present embodiment, store locations for tablets and powder are free, while set locations for tables are fixed.

The medicine packing apparatus comprises tablet storage shelves 1, powder storage shelves 2, packing unit 3, and a control unit 4.

On the tablet storage shelves 1 are stored a large number of tablet cartridges 11.

Figure 2B:
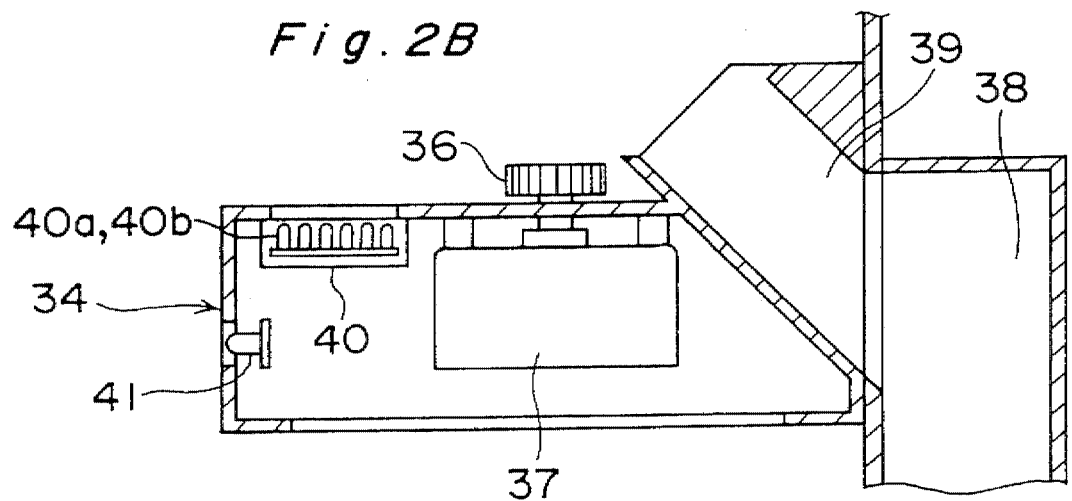
FIG. 2B is a sectional view of a tablet feeder.
Figure 3:
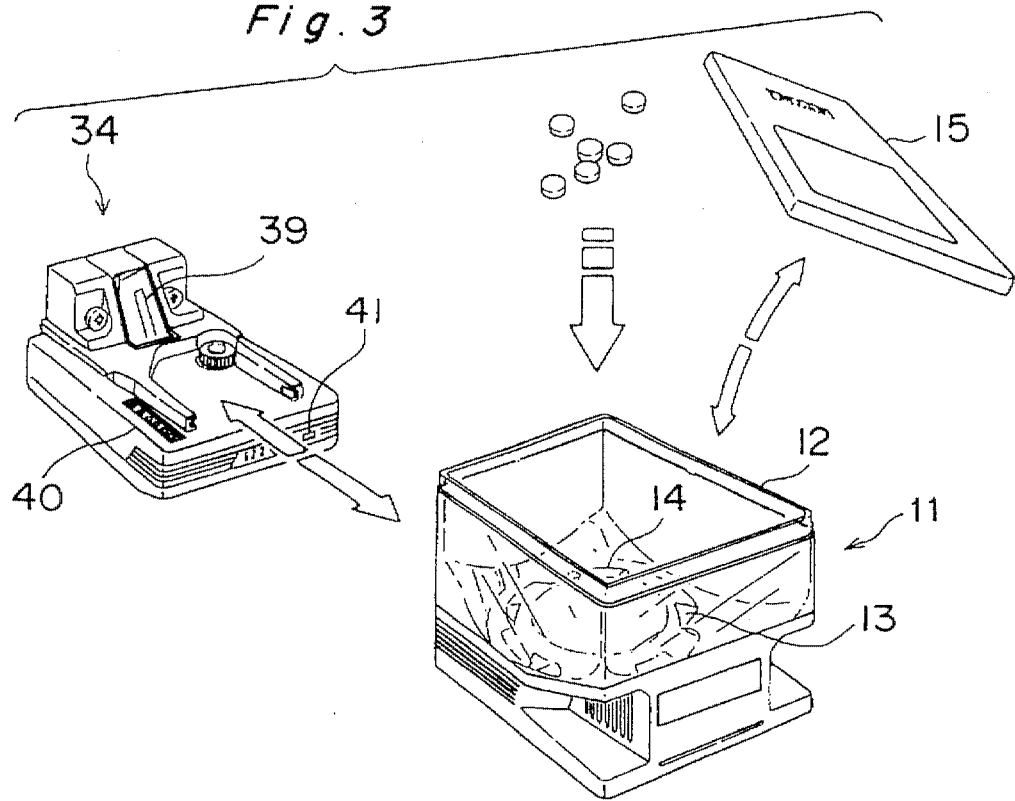
FIG. 3 is a perspective view showing the tablet cartridge and tablet feeder.

Each tablet cartridge 11, as may be seen from FIGS. 2 and 3, comprises a conically bottomed casing 12 for accommodating tablets therein, a rotor 14 rotatably mounted on the bottom of the casing 12 and having a plurality of tablet pockets 13 on the outer periphery thereof, and a cover member 15 for detachably covering the casing 12.

Figure 4:
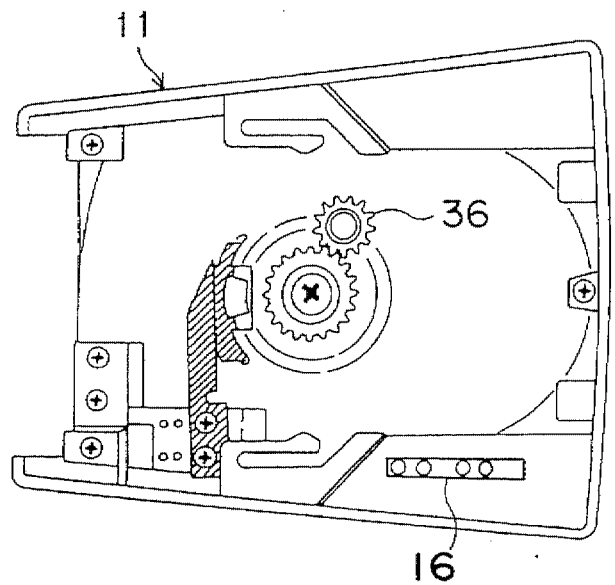
FIG. 4 is a bottom view of the tablet cartridge.

The tablet cartridge 11 is provided with an identification device 16 for identifying internally housed tablets, as shown in FIGS. 2 and 4. The identification device 16 comprises a reflector plate which has reflecting portions and non-reflecting portions (shown by O in FIG. 4) relative to light rays from respective light-emitting elements 17a and 40a of read devices 17 and 40 to be described hereinafter, in order to provide for identification of individual tablets.

As may be seen from FIG. 2A, at each store location in the tablet storage shelves 1, there is embedded a read device 17, with an indicator lamp 18 provided so as to be visually recognizable from the front thereof.

Figure 7:
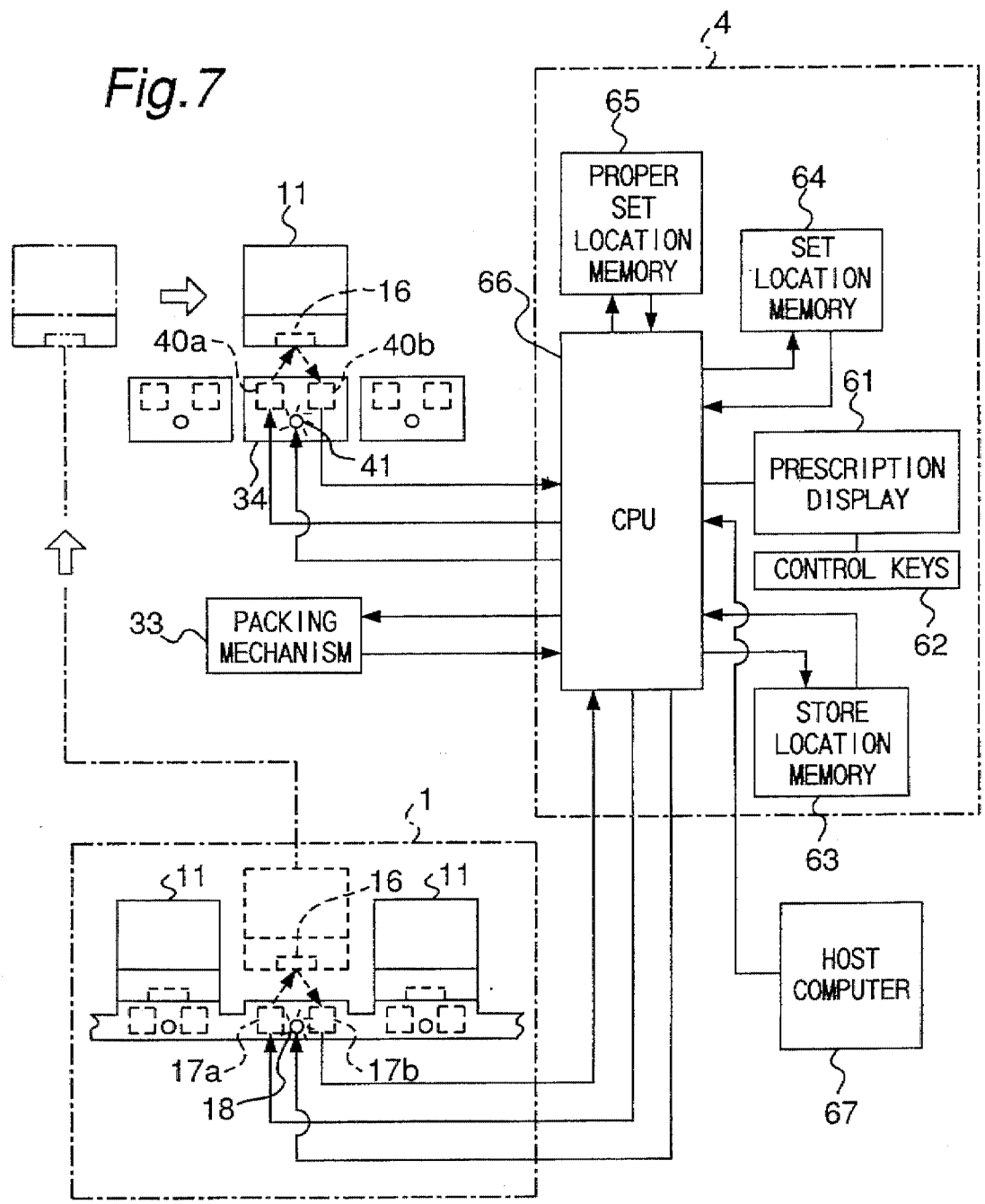
FIG. 7 is a block diagram of a tablet handling operation according to the first embodiment.

The read device 17 constitutes read means of the invention and comprises a plurality of units having light-emitting elements 17a and light-receiving elements 17b which are integrally arranged as a single unit. As FIG. 7 illustrates, the read device 17 operates in such a way that when a tablet cartridge 11 is placed at a given store location, the reflector plate of identification device 16 of the table cartridge 11 reflects light emitted from the light-emitting elements 17a so that the light-receiving elements 17b receives the reflected light, whereby the data on the tablet cartridge can be read.

The indicator lamp 18 constitutes store location indicator means of the invention.

On the powder storage shelves 2 are placed a large number of powder bottles 21 for storage therein.

Figure 5:
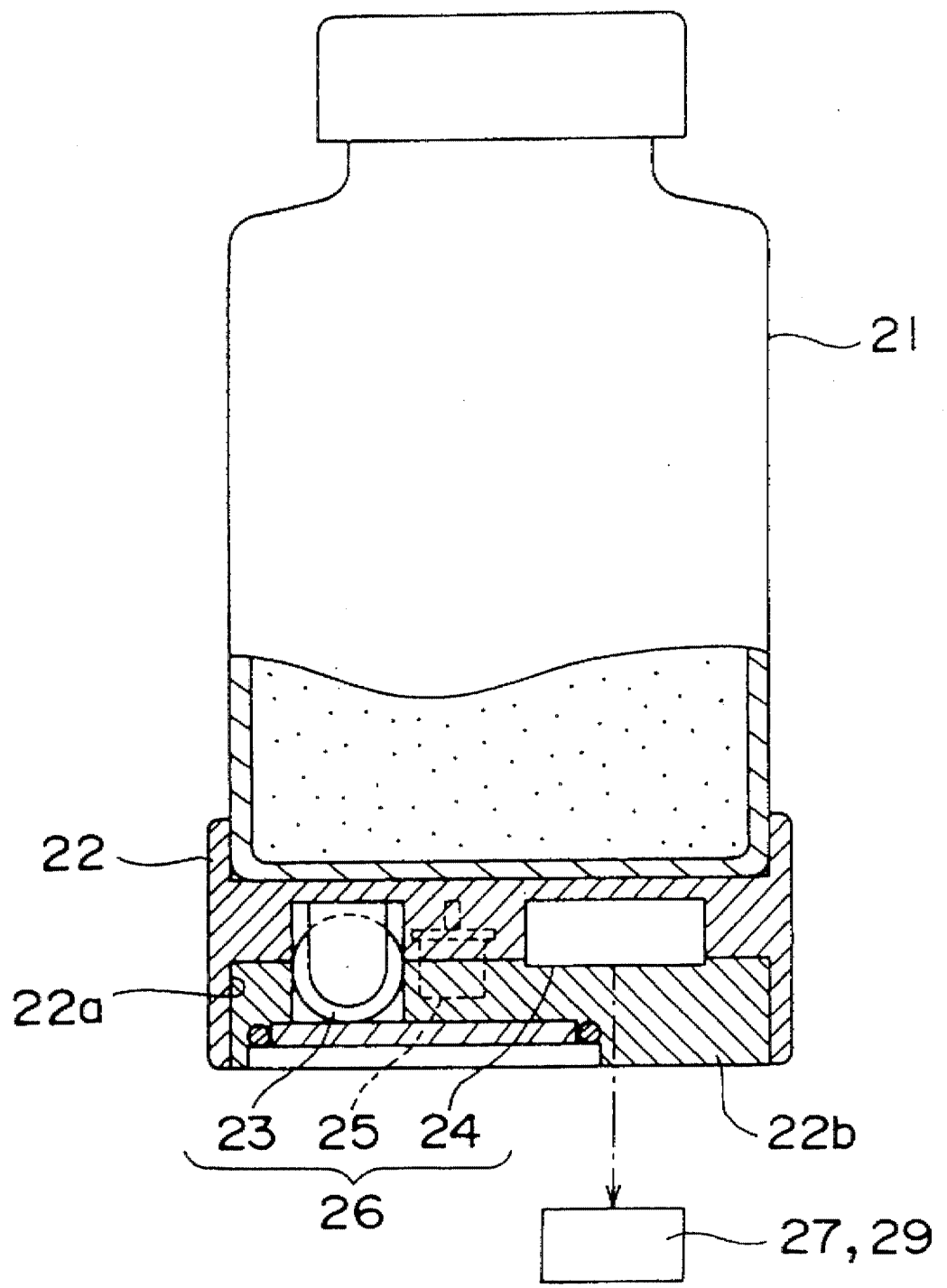
FIG. 5 is a front view, partly in section, of a powder bottle.

Each powder bottle 21 has a seat 22 attached to the bottom thereof as shown in FIG. 5. The seat 22 is provided at its underside with a recess 22a. In the recess 22a is accommodated a powder identification device 26 comprising a battery 23, a signal generator 24 powered by the battery 23, and a switch 25 operative to interrupt a supply line leading from the battery 23 to the signal generator 24. The recess 22a is covered with a cover member 22b.

The switch 25 turns on when the powder bottle 21 is tilted so as to be taken away from the shelf, and turns off when the powder bottle is returned to the shelf. The signal generator 24 has a function to send out an encoded identification signal which represents the name of the powder contained in the powder bottle 21.

Figure 8:
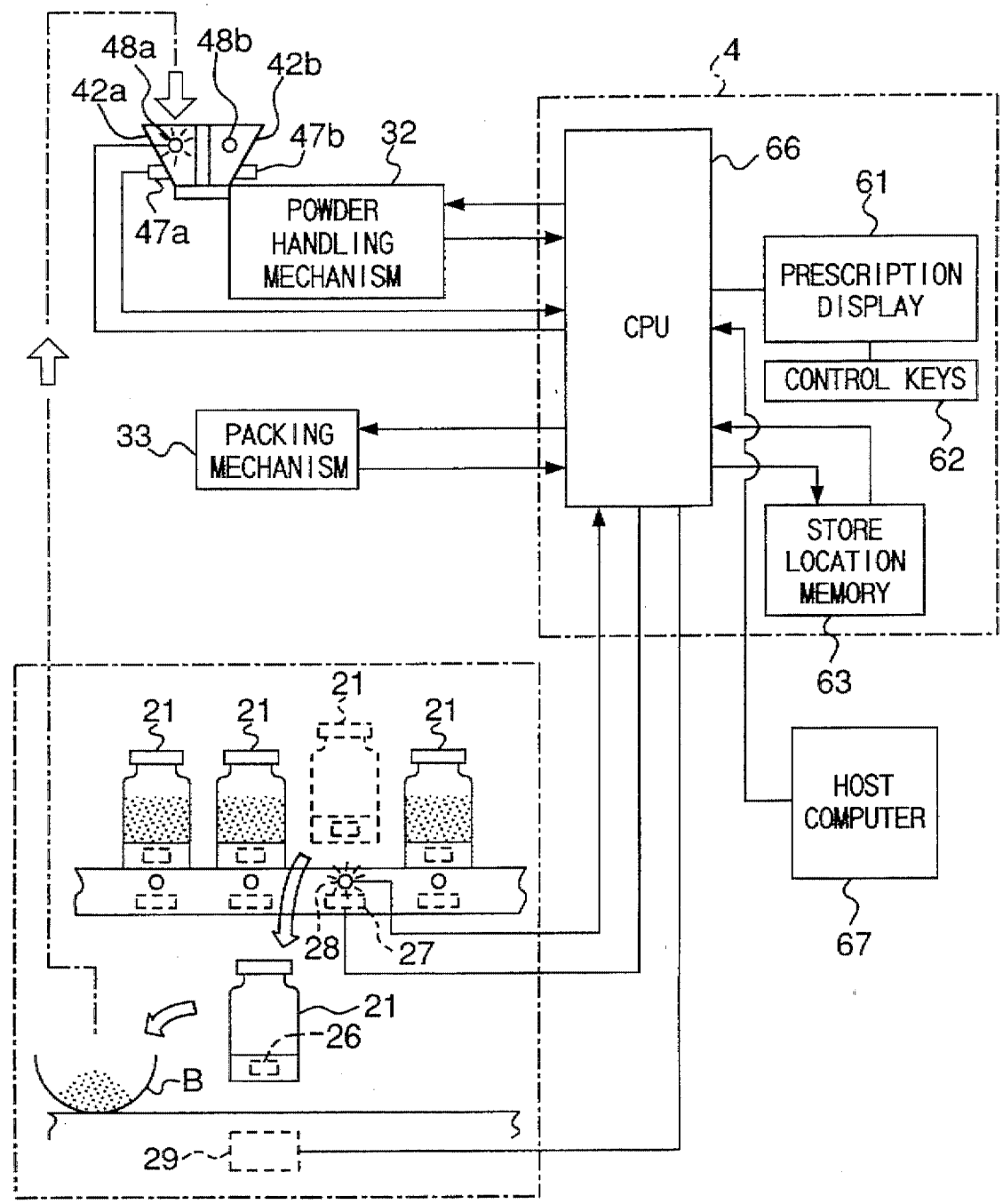
FIG. 8 is a block diagram of a powder handling operation according to the first embodiment.

At individual store locations on each shelf of the powder storage shelves 2, signal receivers 27 are buried under the shelf surface as shown in FIG. 8. Along with the receivers 27 there are disposed indicator lamps 28 which are visible from the front side (see FIG. 1). Each signal receiver 27 constitutes the read means of the invention and is adapted to receive an identification code of the powder bottle 21 sent from the signal generator 24 so as to read relevant powder data when the powder bottle 21 is placed at a store location. The indicator lamp 28 constitutes the store location indicator means of the invention.

On a table portion of the powder storage shelves 2, as FIG. 1 illustrates, there are placed a bowl (mortar and pestle) B and a scale M for powdered medicine. Under the table surface are embedded a signal receiver 29. The signal receiver 29 constitutes the read means of the invention.

Figure 6:
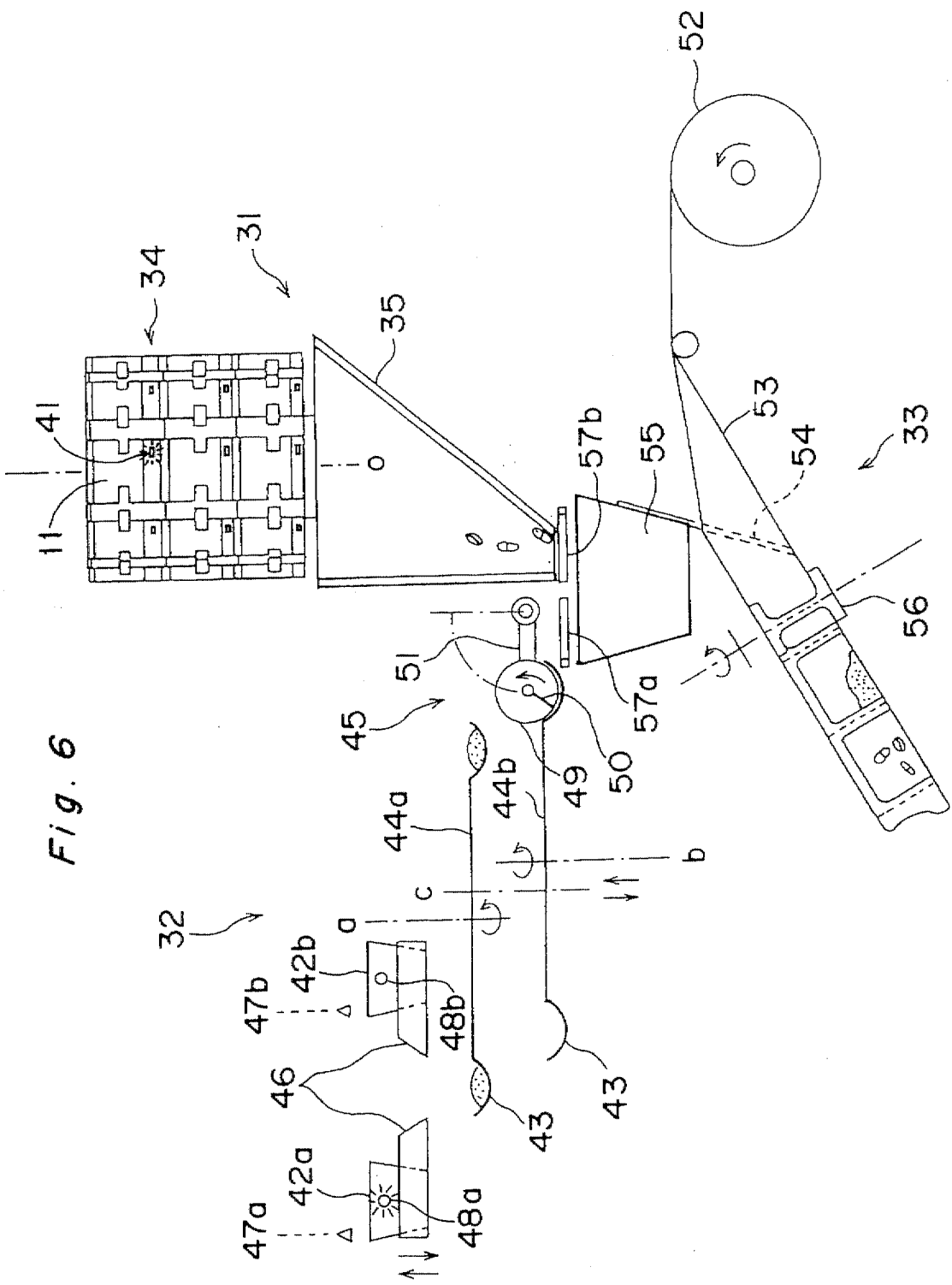
FIG. 6 is schematic view showing a powder handling mechanism, a tablet handling mechanism, and a packing mechanism.

The packing unit 3 comprises a tablet handling mechanism 31, a powder handling mechanism 32, and a packing mechanism 33 as shown in FIG. 1 and FIG. 6.

The tablet handling mechanism 32 comprises a plurality of tablet feeders 34 and a tablet hopper 35.

The tablet feeders 34, in their entirety, define a cylindrical feeder assembly such that the tablet feeders 34 are annularly arranged about a rotation axis o and are stacked vertically in a plurality of tiers. The tablet feeders 34 are rotatable about the rotation axis o. Each tablet feeder 34 is adapted to be loaded with a tablet cartridge 11 which has been stored in the tablet storage shelves 1. There is provided a relatively small number of tablet feeders 34 such that only necessary tablet cartridges 11 are set on the tablet feeders 34. A majority of tablet cartridges 11 is stored in the tablet storage shelves 1.

Each tablet feeder 34 is provided with a drive motor 37 to which the shaft of a rotor 14 of a tablet cartridge 11 is connected through a gear 36 when the tablet cartridge 11 is set in position, and a chute 39 which directs each tablet to a central passageway 38 as the tablet is discharged from the cartridge 11.

Each tablet feeder 34 is also provided with a read device 40 disposed at a position corresponding to that of the identification device 16 of the cartridge 11 for reading relevant tablet data from the identification device 16, and an indicator lamp 41. The read device 40 constitutes read means of the invention and is of the same construction as the read device 17 of the tablet storage shelves 1 shown in FIG. 2A. The read device 40 comprises a plurality of units having light-emitting elements 40a and light-receiving elements 40b which are integrally arranged as a single unit, such that the light-emitting elements 40a emit light toward a reflector plate of the identification device 16 of the tablet cartridge 11 when the tablet cartridge 11 is mounted to the tablet feeder 34, and the light-receiving elements 40b receive the light reflected from the reflector plate. The indicator lamp 41 constitutes set location indicator means of the invention.

The tablet hopper 35, as FIG. 6 shows, directs tablets fed from the tablet feeder 34 to a packing hopper 55 of the packing mechanism 33 which will be described hereinafter.

The powder handling mechanism 32, as FIG. 6 shows, comprises two powder hoppers 42a, 42b, two distributing boards 44a, 44b each having a distributing tray 43 defined by an annular groove extending along its outer circumferential edge, and a divider 45.

The powder hoppers 42a, 42b each include a chute 46 which oscillates vertically so as to enable the powder poured into the powder hoppers to be equally fed onto the distributing trays 43 of the distributing boards 44a, 44b. The powder hoppers 42a, 42b and their respective chutes 46 are adapted to move upward and downward so as to supply the powder to the distributing tray 43 of one of the distributing boards 44a, 44b. Each of the powder hoppers 42a, 42b is equipped with a sensor 47a; 47b for detecting its availability, and an indicator lamp 48a; 48b for indicating the hopper in which the powder can be poured.

The two distributing boards 44a, 44b are disposed one over the other and are each independently rotatable about a rotation axis a; b. Further, they are pivotable about a common pivot axis c provided intermediate the axis a and b and are also vertically movable in integral relation. Through this arrangement the distributing trays 43 are movable to a distributing position at which the respective trays 43 are positioned at one end below the respective powder hoppers 42a, 42b so that powder fed through the powder hopper 42a, 42b is distributed over the distributing tray 43, and to a dividing position at which the respective trays 43 are positioned at one end below the divider 45 so that the powder on the distributing tray 43 may be scraped out by the divider 45 by constant divisions.

The divider 45 comprises a disc 49 having a diameter matching the curve of respective distributing trays 43 of the distributing boards 44a, 44b, a scrape-out plate 50 disposed on the front of the disc 49, and an arm 51 operative to pivot the disc 49 for movement between a position at which it is received in one of the distributing trays 36 and a position at which the disc 49 is held away therefrom. The disc 49 is also drivable for rotation about its axis.

The packing mechanism 33, as may be seen from FIG. 6, is such a mechanism as described hereinafter. Packing paper 53 drawn from a roll 52 is longitudinally folded in two with the aid of a triangular plate 54. In the folded portion is received tablets or powder by one dose fed from the tablet handling mechanism 31 or powder handling mechanism 32 via the packing hopper 55. Then, sealing is performed by a heat sealing device 56 along three side edges other than the folded portion to complete packing. The packed portion is discharged outwardly.

The packing hopper 55 is provided at its open top portion with doors 57a, 57b for temporarily holding powder discharged from the divider 45 of the powder handling mechanism 32, and tablets discharged from the tablet handling mechanism 31, respectively.

The control unit 4 comprises a prescription display 61 with control keys 62, a store location memory 63, a set location memory 64, a proper set location memory 65, and a central processing unit (CPU) 66.

The prescription display 61 displays prescription data according to a prescription input from a host computer 67 to CPU 66.

The control keys 62 are to change, at an operator's own discretion, the sequence of packing displayed on the prescription display 61.

The store location memory 63 memorizes data on the store location of each tablet cartridge 11 in the tablet storage shelves 1 (see FIG. 7), and on the store location of each powder bottle 21 in the powder storage shelves 2 (see FIG. 8).

The set location memory 64 memorizes data on the set location for the tablet cartridge 11, i.e., the particular tablet feeder 34 on which each tablet cartridge 11 is set.

Tablets have particular attributes, such as bouncing characteristic when dropped, sliding characteristics relative to inclined plane, and rolling characteristics, so that the time required in travelling from the set position to the packing position differs according to the type of the tablet, which has some effect upon the speed of packing. In the present embodiment, the proper set location memory 65 memorizes a proper set location (as viewed in a vertical direction) preset according to the attributes of individual types of tablets.

The central processing unit (CPU) 66 manages store and set locations for tablet cartridges 11 and powder bottles 21, and actuates the tablet handling mechanism 31, powder handling mechanism 32 and packing mechanism 32 according to the sequence of packing displayed on the prescription display 61.

The operation of the CPU 66 will now be explained with reference to the flow chart given in FIGS. 9 and 10.

Figure 9:
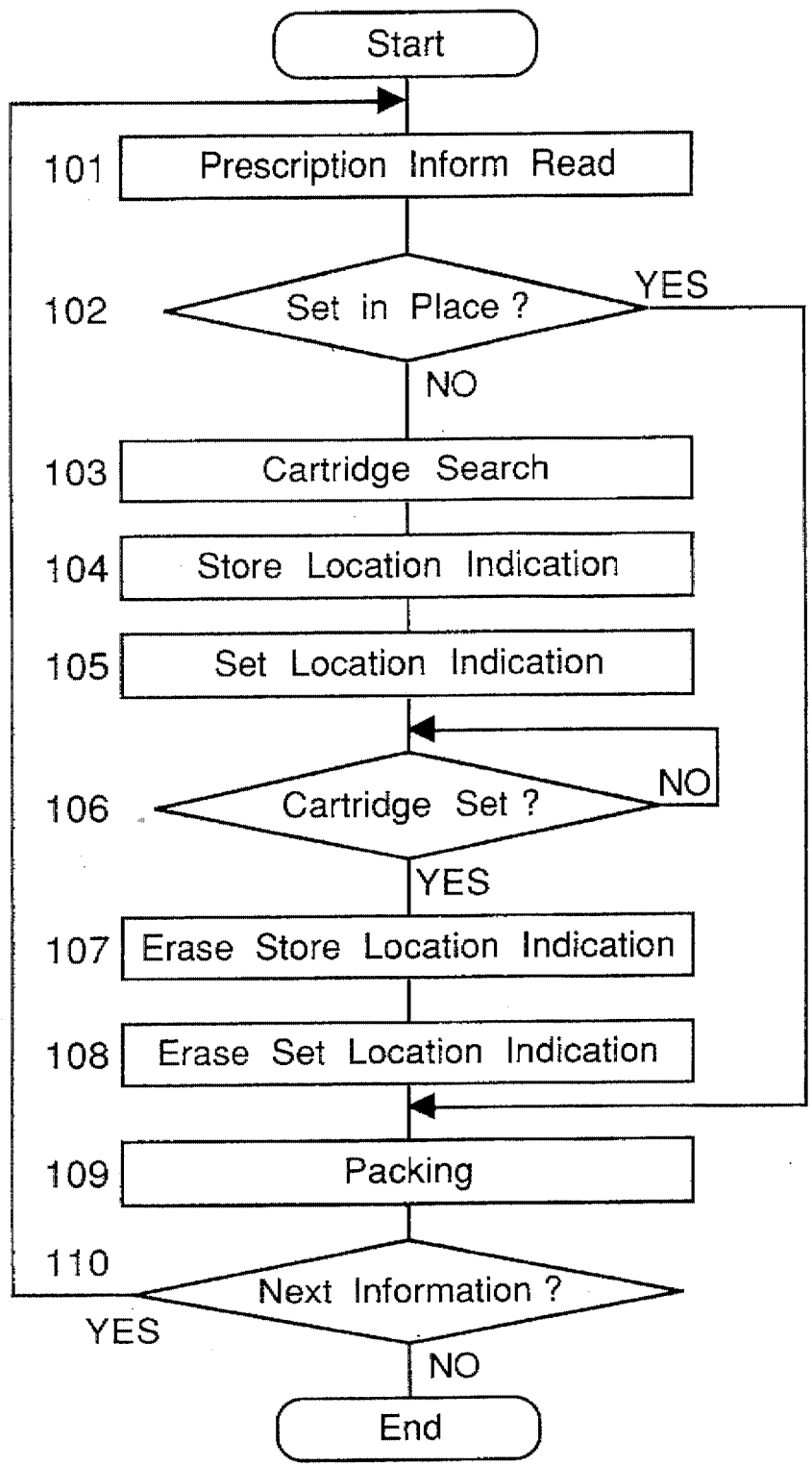
FIG. 9 is a flow chart of the tablet handling operation according to the first embodiment.

FIG. 9 shows the operation of CPU 66 with respect to a tablet prescription.

At step 101, CPU reads prescription information. At step 102, CPU inquires of the set location memory 64 about the set location of a tablet cartridge 11 corresponding to the prescription and then judges whether the tablet cartridge 11 is set on any of tablet feeders 34. If the tablet cartridge 11 is not set in position, at step 103 an inquiry is made of the store location memory 63 to search the store location of the tablet cartridge 11. At step 104, the indicator lamp 18 for the searched store location is caused to light to indicate the store location for the tablet cartridge 11. At step 105, the indicator lamp 41 of the tablet feeder 34 is caused to light to thereby indicate a set location suited to the tablet prescription.

Then, an operator (dispenser) takes out from the tablet storage shelves 1 the tablet cartridge 11 at the indicated location and set the same in the tablet feeder 34 at the indicated location, whereupon the tablet data at the identification device 16 of the tablet cartridge 11 is read by the read device 40 of the tablet feeder 34 so that the tablet data and set location of the tablet cartridge 11 are recorded in the set location memory 64.

At step 106, an inquiry is made again of the set location memory 64 in order to judge whether the corresponding tablet has been set in position. If the tablet has not been set, CPU waits until the tablet has been set. If the tablet has already been set, at step 107, the indication of the store location is erased, and at step 108 the indication of the set location is erased. At step 109, packing is carried out.

If, at step 102, the tablet corresponding to the prescription has already been set in position, display may be skipped and the program may proceed directly to step 109 for packing.

If, at step 110, there is next prescription information, CPU returns to step 101 to repeat the foregoing steps. If there is no such information, the task ends.

Figure 10:
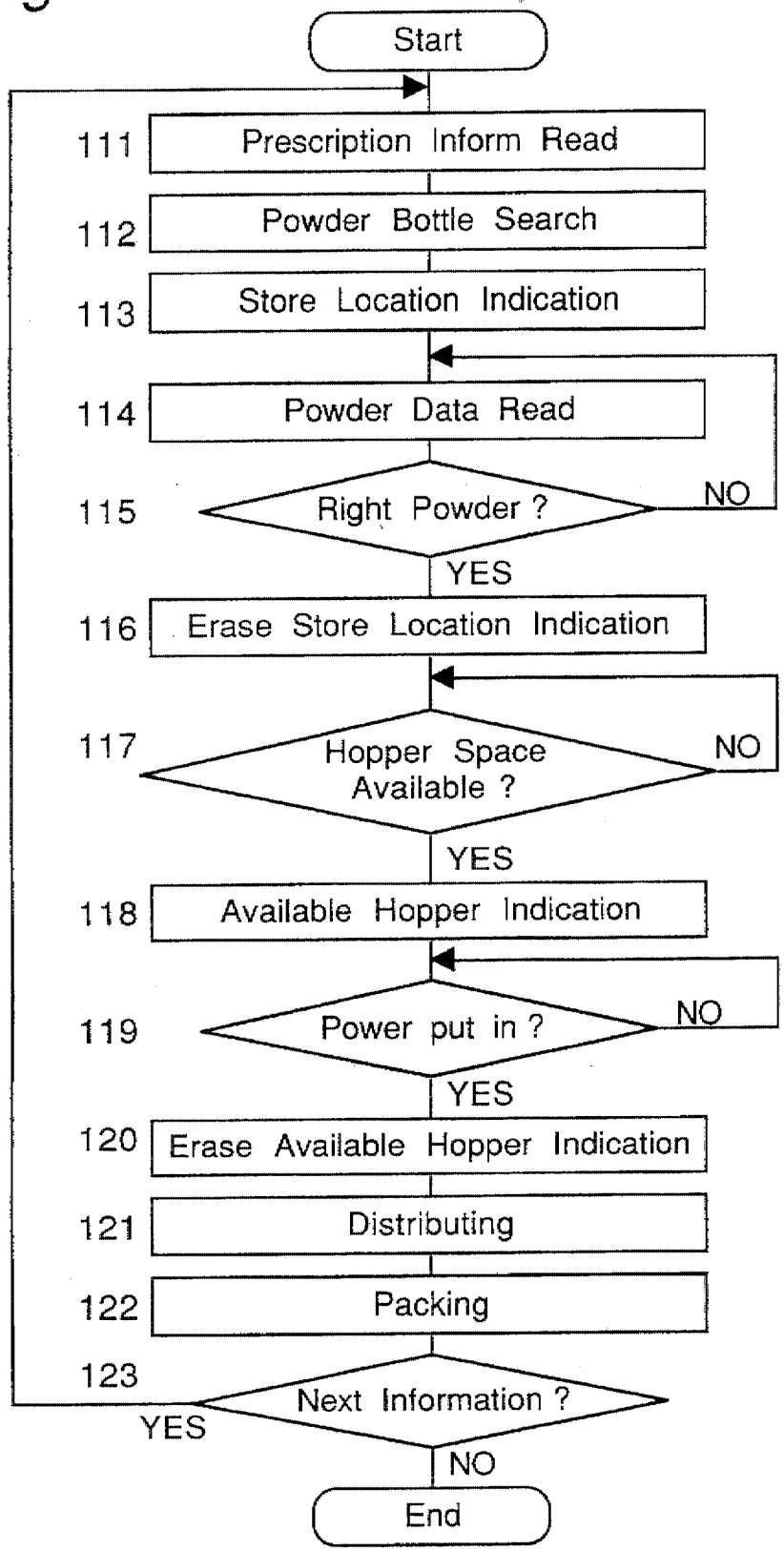
FIG. 10 is a flow chart of the powder handling operation according to the first embodiment.

FIG. 10 shows the operation of CPU 66 with respect to a powder prescription.

CPU reads prescription information at step 111 and makes an inquiry of the store location memory 63 for search of the store location of the corresponding powder bottle 21 at step 112. At step 113, the indicator lamp 28 for the searched store location is caused to light, whereby the store location of the powder bottle 21 is indicated.

When the operator takes out the powder bottle 21 at the indicated shelf and places the same at a predetermined location on the table, CPU 66, at step 114, causes read device 29 to read the powder data on the powder bottle 21. At step 115, the powder data is checked as to whether or not the powder corresponds to the prescription. If the powder is not the right powder, CPU returns to step 114 to wait until the right powder bottle is taken out. If the powder is right, the indication of the store location is erased at step 116.

Then, at step 117, on the basis of signals from sensors 47a, 47b, judgement is made as to whether or not any hopper space is available. If no hopper space is available, CPU keeps itself on a standby position. If any hopper space is available, at step 118 indicator lamps 48a, 48b of the space available hopper are caused to light thereby to indicate the available hopper.

At this time point, the operator may dispense powders taken out using scales M and place the powder in the bowls B, which in turn may be introduced into the indicated hopper.

At step 119, on the basis of signals from sensors 47a, 47b, judgement is made as to whether or not the powder has been put into the hopper. If the powder has not been put in, CPU waits until the powder has been put into the hopper. If the powder has been put in, the indication of hopper availability is erased at step 120.

At step 121, the powder handling mechanism 32 is actuated to distribute the powder, and at step 122 the divider 45 and packing mechanism 33 are driven to perform packing.

At step 123, if there is next prescription information, CPU returns to step 111 to repeat the foregoing steps. If there is no such information, the task ends.

In the above described first embodiment, store locations for tablets and powders are free. Therefore, it is possible to place any tablet cartridge 11 or powder bottle 21 taken out, at a lower and nearer location as desired. The indication of store location with respect to any tablet or powder corresponding to a prescription permits ready removal of the tablet or powder from the store location. In addition, the indication of a set location suited to the attributes of a tablet involves no doubt as to the location at which the tablet is to be set.

For powder handling in the first embodiment, it is arranged that the operator may dispense a powder by himself and put it into a hopper. However, it is possible to automate this process as in the case of tablet handling. For this purpose, powder cartridges of substantially same construction as tablet cartridges 11, and powder feeders adapted to be removably loaded with such powder cartridges and capable of discharging powder in a quantity corresponding to relevant prescription may be provided in pluralities. In this case, the identification of any powder cartridge may be made in the entirely same way as in the case of tablet cartridge identification in the first embodiment.

(2) Second Embodiment

Figure 11:
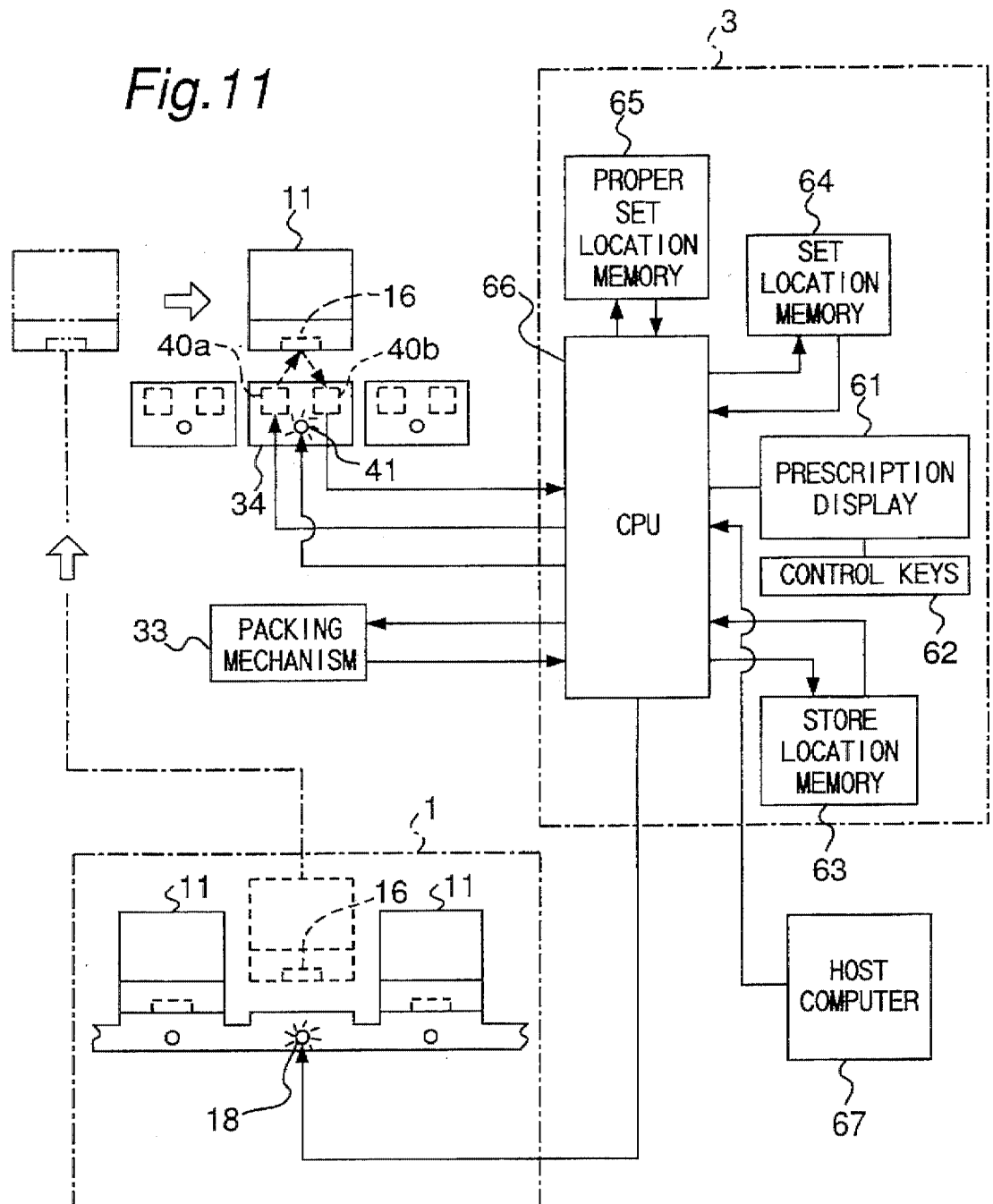
FIG. 11 is a block diagram of a tablet handling operation according to a second embodiment.

FIG. 11 shows an example in which store locations for tablets are previously fixed and set locations for them are also fixed.

In the present embodiment, no such read device for tablet cartridge 11 as in the first embodiment is provided at each store location in the tablet storage shelves 1, and tablets to be stored at individual store locations are previously recorded in the store location memory 63. It is arranged that a store location for a particular tablet corresponding to a prescription is to be indicated by an indicator lamp 18.

The manner of operation of CPU in this embodiment is same as that shown in FIG. 9. Therefore, description in that respect is omitted.

The store location for each type of powder may be likewise fixed.

(3) Third Embodiment

Figure 12:
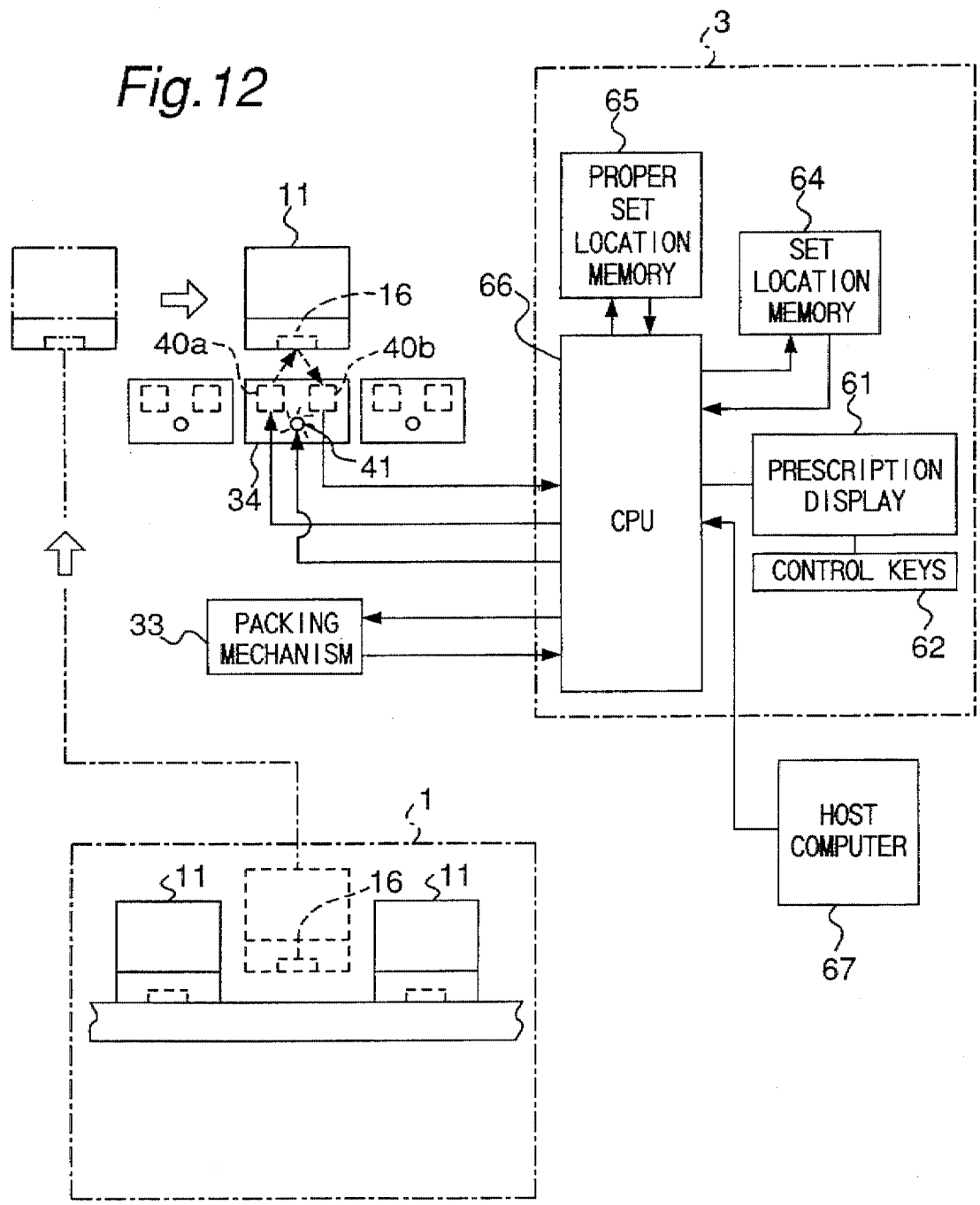
FIG. 12 is a block diagram of a tablet handling operation according to a third embodiment.

FIG. 12 shows an example in which store locations for tablets are free, while set locations for them are fixed. Although neither control nor indication is made with respect to such store location, it is arranged that the number for a particular tablet cartridge 11 corresponding to a prescription is to be only indicated on the prescription display 61. Therefore, the tablet storage shelves 1 of the present embodiment are not provided with such read device or indicator lamp as in the first embodiment. There is no provision of store location memory either.

Figure 13:
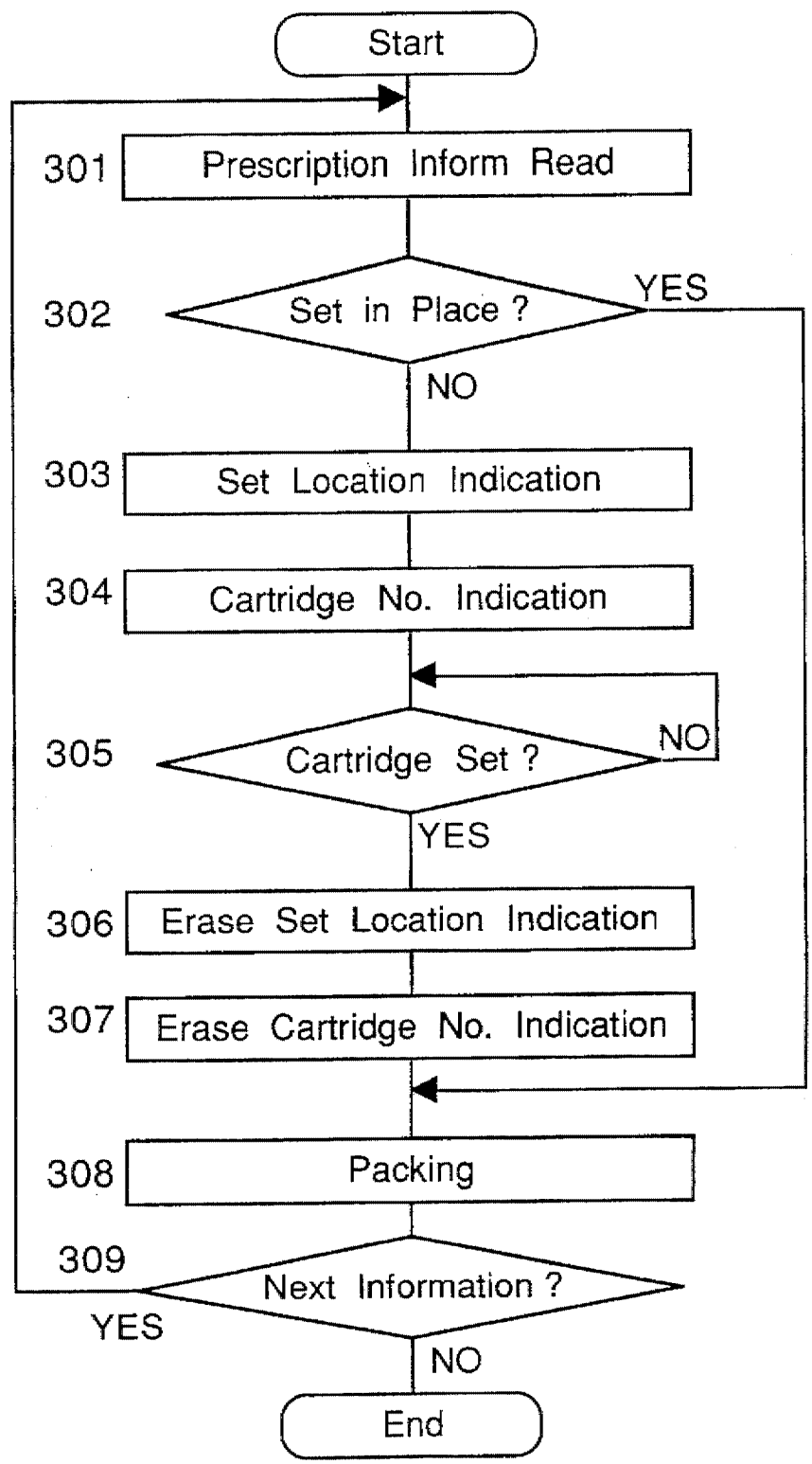
FIG. 13 is a flow chart of the tablet handling operation according to the third embodiment.

The operation of CPU 66 in the present embodiment will be explained with reference to the flow chart given in FIG. 13. At step 301, CPU reads prescription information, and at step 302 judgement is made as to whether or not a tablet cartridge 11 corresponding to the prescription has been set on a tablet feeder 34. If the tablet cartridge 11 is not set, at step 303 a set location suited to the attributes of the tablet is indicated and, at step 304, cartridge number of the tablet is given on the prescription display 61.

Accordingly, the operator may search the tablet cartridge having the number indicated on the prescription display 61 to take out from the tablet storage shelves 1, and may set the same in a tablet feeder 34 at the indicated set location.

Then, at step 305, CPU 66 waits until the tablet cartridge 11 is set in position, and after the tablet cartridge 11 is so set, the indication of the set location is erased at step 306. At step 307, the indication of the cartridge number is erased, and at step 308 packing is carried out.

At step 309, if there is any subsequent information, CPU returns to step 301 for repetition of the foregoing steps. If there is no next information, the process is terminated.

Also with respect to powder bottles 21, it may be arranged that store locations are free with no display or control thereof being made, and that only the relevant powder bottle number is indicated so that the operator can search the powder bottle by himself.

(4) Fourth Embodiment

Figure 14:
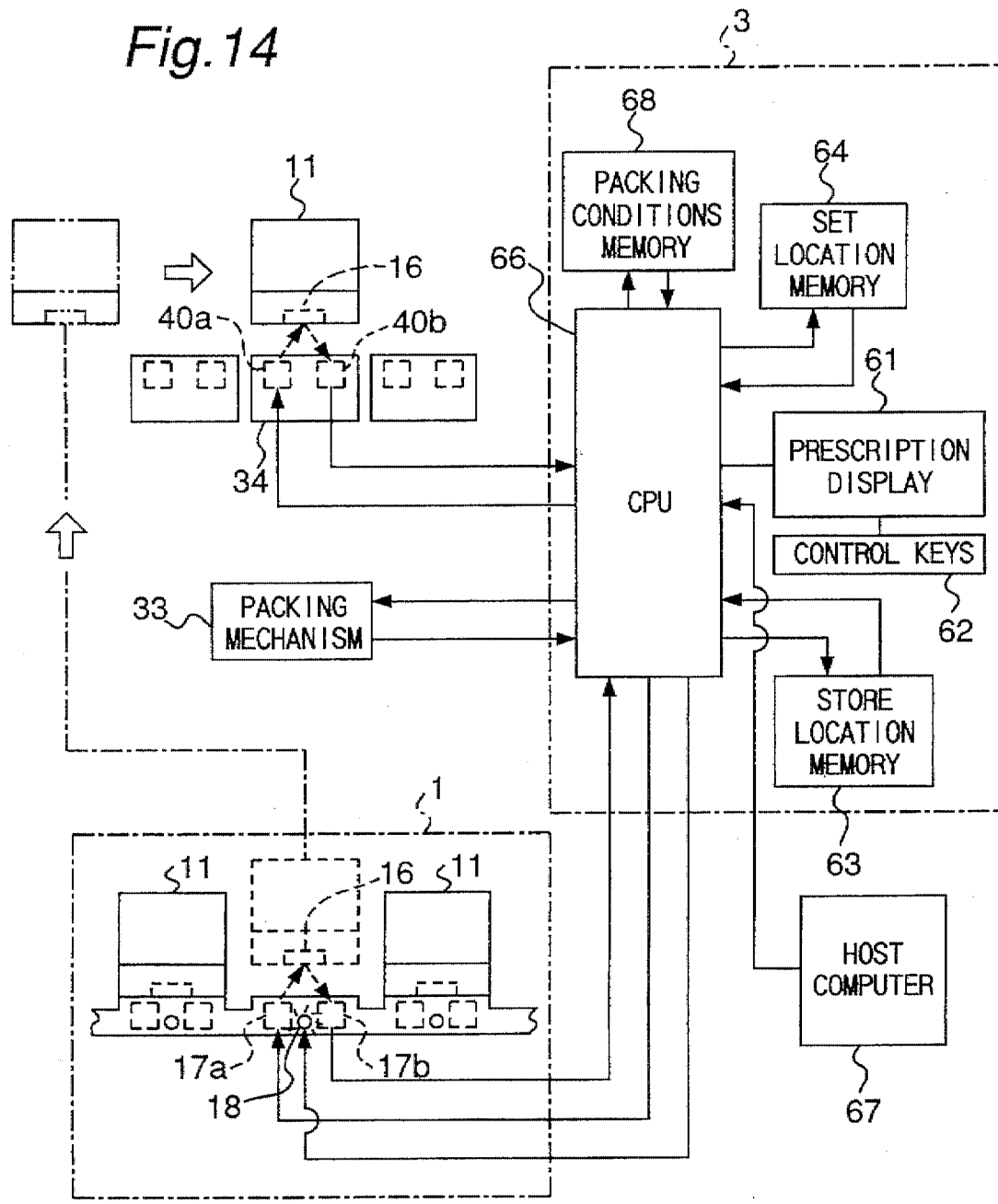
FIG. 14 is a block diagram of a tablet handling operation according to a fourth embodiment.

FIG. 14 shows an example of apparatus in which store locations for tablets are free and set locations for them are not fixed. Therefore, free setting of tablets are possible.

The apparatus of this embodiment is of the same arrangement as the first embodiment shown in FIG. 7, except that each tablet feeder 34 has no indicator lamp and that a packing conditions memory 68 is provided instead of the proper set location memory.

The operation of CPU 66 in the present embodiment will be explained with reference to the flow chart given in FIG. 15. At step 401, CPU reads prescription information, and at step 402 an inquiry is made of the set location memory 64 to decide whether or not the relevant tablet cartridge 11 has been set in position. At step 403 an inquiry is made of the store location memory 63 in order to search the tablet cartridge 11 corresponding to the prescription. At step 404, the searched store location is indicated by indicator lamp 18.

The operator takes out the tablet cartridge 11 at the indicated store location and set the same in a tablet feeder 34 at a free location, whereupon the identification device 16 of the tablet cartridge 11 at the set location is read by the read device 40 so that the set location is recorded in the set location memory 64.

At step 405, CPU 66 again inquires of the set location memory 64 about whether or not the set location for the subject tablet cartridge 11 has been recorded therein, thereby to judge whether or not the cartridge 11 has been set in position. If the cartridge 11 has not yet been set, then CPU waits until the cartridge is set. If it is already set, the indication of the set location is erased at step 406.

Then, at step 407, CPU inquires of the packing conditions memory 68 in order to select packing conditions compatible with the attributes of the tablets contained in the tablet cartridge 11 and the set location of the cartridge. In the case where a tablet is likely to bounce, if the set location is relatively high, a low packing velocity is selected, because the tablet bounces high so that more time is required until the tablet reaches a packing position. Conversely, if the set location is relatively low, a faster packing velocity is selected.

(5) Fifth Embodiment

Figure 16:
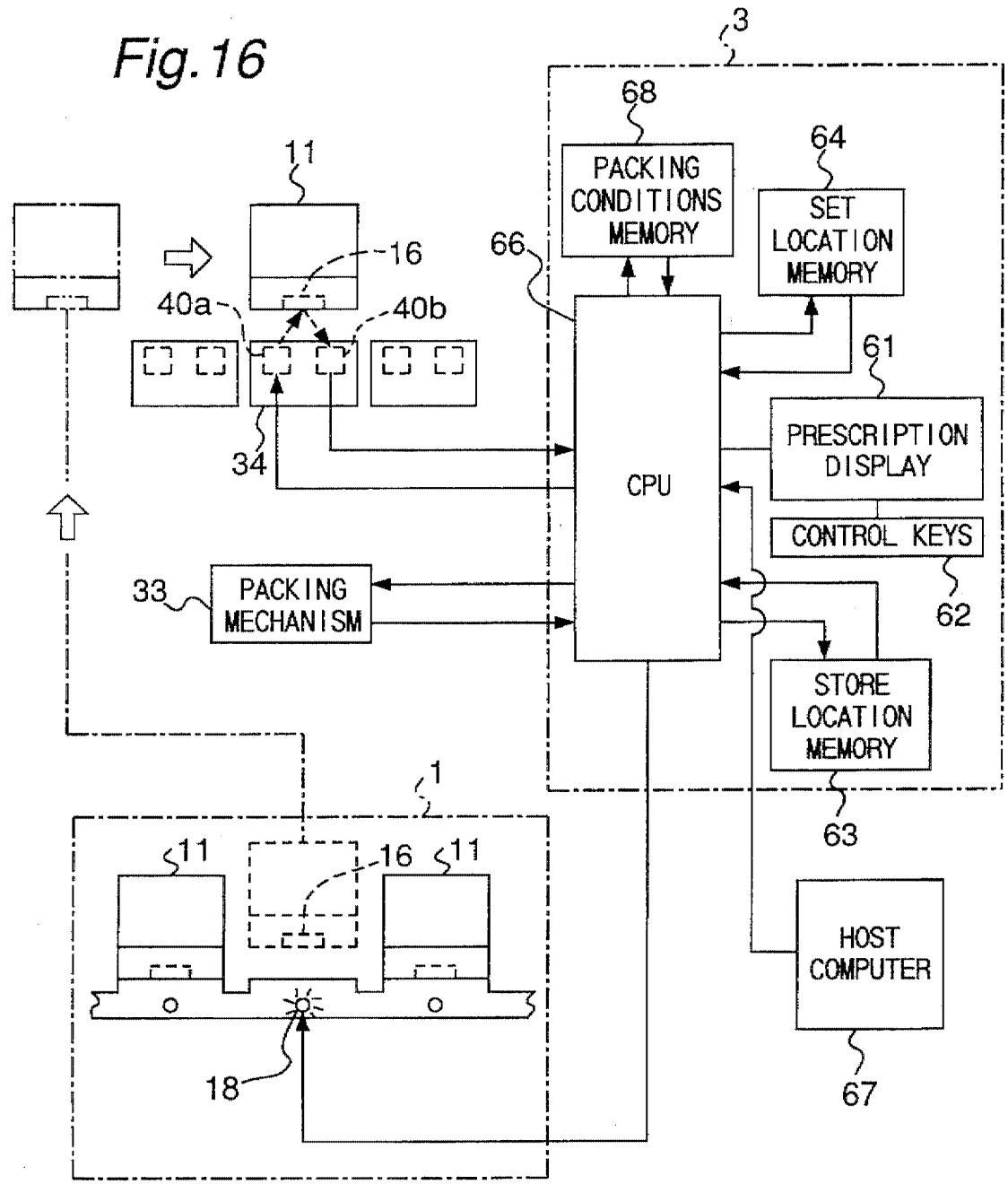
FIG. 16 is a block diagram of a tablet handling operation according to a fifth embodiment.

FIG. 16 shows an example in which store locations for tablets are previously fixed, while set locations therefor are not fixed.

In the present embodiment, there is no provision of a read device for tablet cartridge 11 at each store location in the tablet storage shelves 1, and the particular tablet to be stored at each respective store location has been previously recorded in the store location memory 63. The store location for a tablet corresponding to a prescription is to be indicated by indicator lamp 18.

Figure 15:
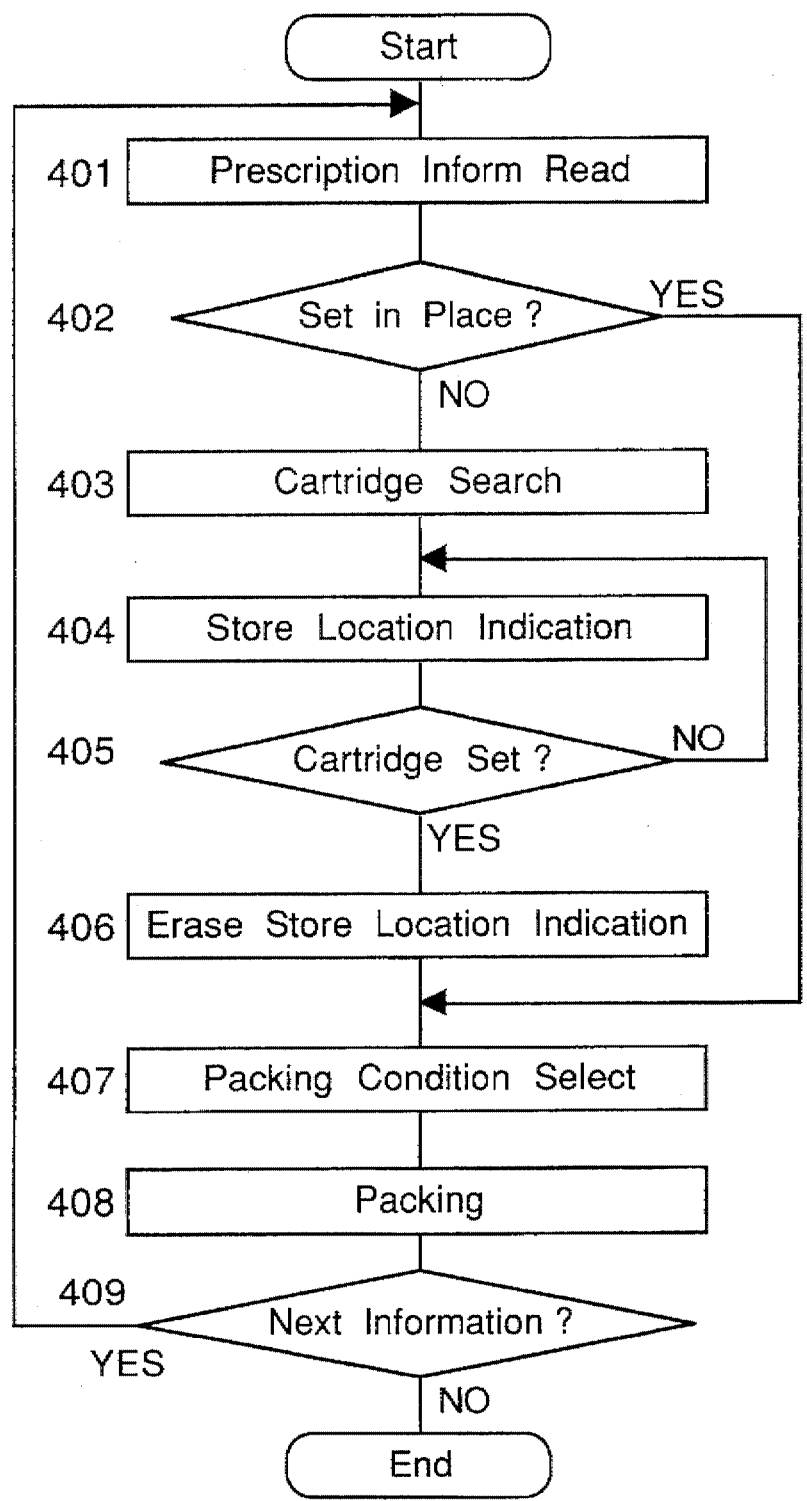
FIG. 15 is a flow chart of the tablet handling operation according to the fourth embodiment.

The manner of operation of CPU 66 in this embodiment is same as that shown in FIG. 15. Therefore, explanation thereof is omitted.

(6) Sixth Embodiment

Figure 17:
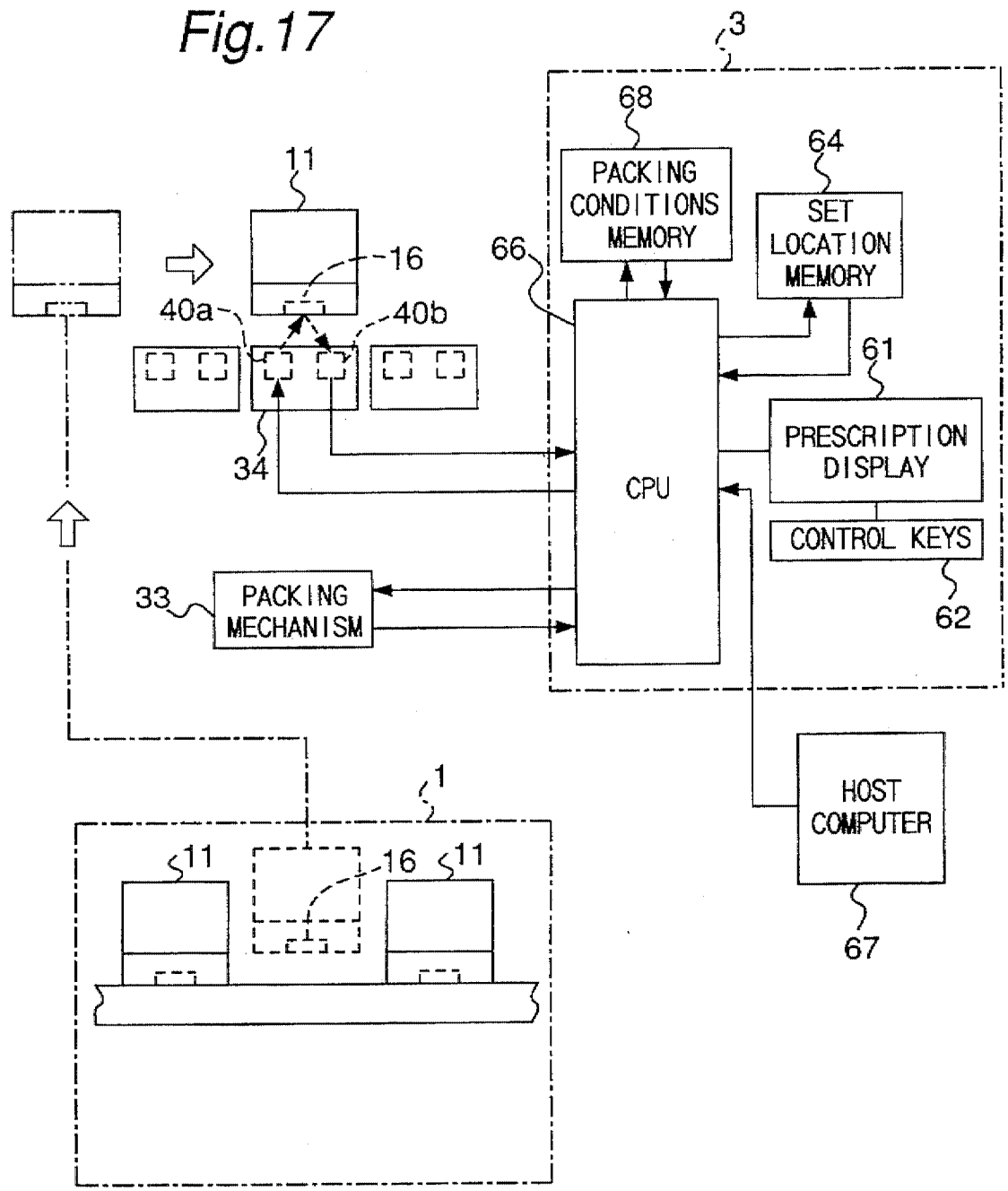
FIG. 17 is a block diagram of a tablet handling operation according to a sixth embodiment.

FIG. 17 shows an example in which store locations for tablets are free and set locations for them are also free. While neither control nor indication is made with respect to such tablet store locations, the number of the tablet cartridge 11 corresponding to a prescription is simply indicated on the prescription display 61. In the apparatus of this embodiment, therefore, the tablet storage shelves 1 is provided with no such means as those used in the fourth embodiment, such as read device and indicator lamps. No store location memory is provided either.

Figure 18:
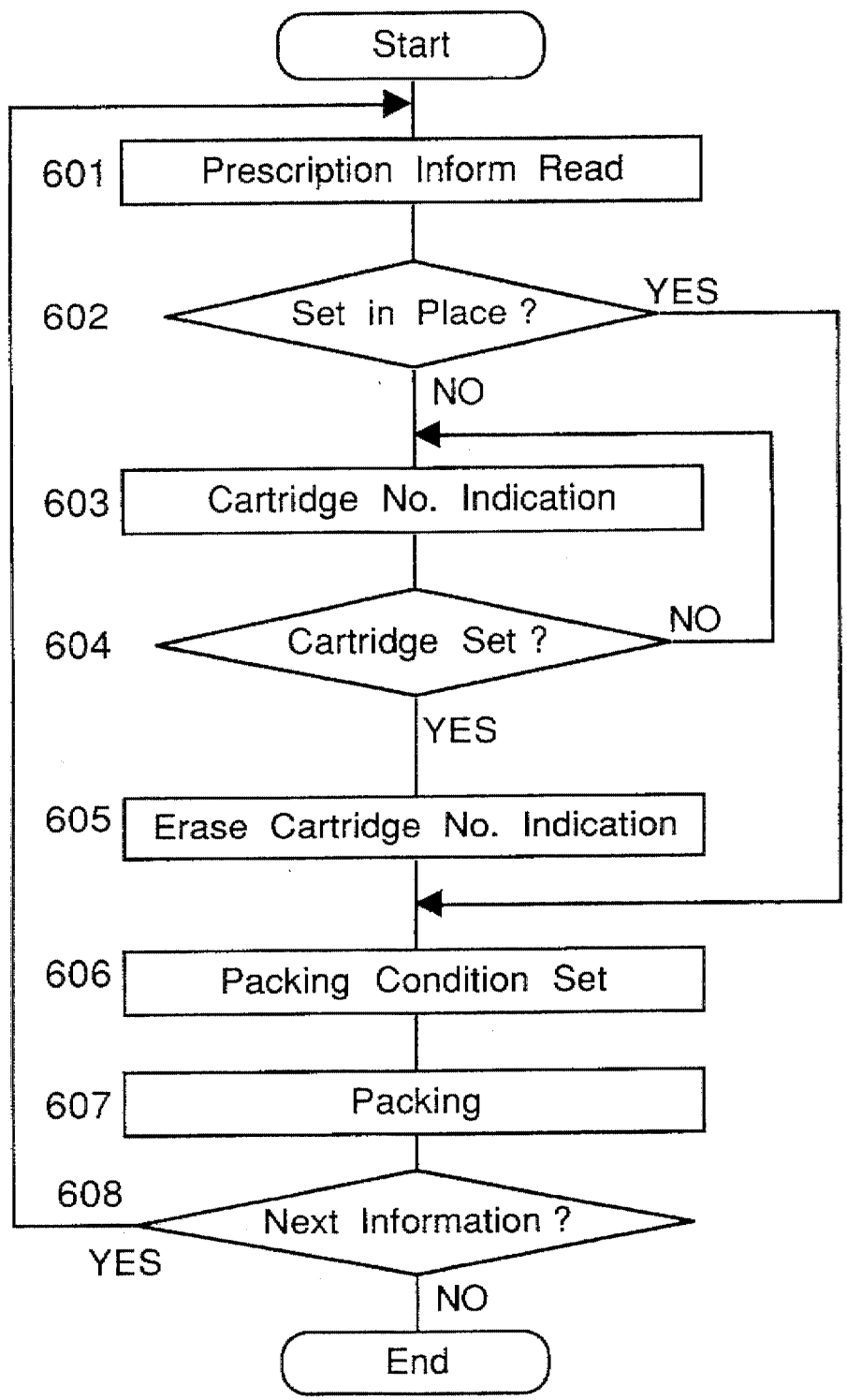
FIG. 18 is a flow chart of the tablet handling operation according to the sixth embodiment.

The manner of operation of CPU 66 in this embodiment is explained with reference to the flow chart given in FIG. 18. At step 601, CPU reads prescription information, and at step 602 judgement is made as to whether or not a tablet cartridge 11 corresponding to a prescription has been set on a tablet feeder 34. If the tablet has not yet been set, the cartridge number of the corresponding tablet is indicated on the prescription display 61 at step 603.

Accordingly, the operator may search the tablet cartridge 11 having the cartridge number indicated by the prescription display 61 to take out the same from the tablet storage shelves 1, and then set the tablet cartridge 11 in any selected tablet feeder 34. Thus, the identification device 16 of the tablet cartridge 11 is read by read device 40 at the set location, and the set location is recorded in the set location memory 64.

Then, at step 604, CPU again inquires of the set location display 64 as to whether or not the tablet cartridge 11 has been set, and if the cartridge has not been set, CPU waits until the cartridge is set. If the cartridge has been set, at step 605 the indication of the cartridge number is erased. At step 606, packing conditions compatible with the attributes of the tablet and the set location of the cartridge are selected in the same way as in the fifth embodiment, and at step 607 packing is carried out.

At step 608, if there is any subsequent information, CPU returns to step 601 for repetition of the foregoing steps. If there is no further information, the job ends.

(7) Examples of Identification Means for Tablet Cartridge and Powder Bottles

In the foregoing embodiments, identification of the tablet cartridge 11 is made by means of the read device comprising light-emitting elements 17a and light-receiving elements 17b disposed at the tablet storage shelves 1, or the read device 40 comprising light-emitting elements 40a and light-receiving elements 40b disposed in the tablet feeder 34, and the reflector plate 16 disposed in the tablet cartridge 11, in combination. Identification of a powder bottle 21 is made by means of the signal receiver 27 disposed at the store location for the powder bottle 21 or the signal receiver 29 disposed on the table, and the signal generator 24 disposed in the powder bottle 21, in combination.

Besides these means, various types of identification means enumerated hereinbelow may be utilized. In this connection, the tablet storage shelves 1, tablet feeders 34, and powder storage shelves 2 are referred to as a stationary side, and tablet cartridges 11 and powder bottles 21 placed on or set on these members are simply referred to as a container side.

(a) Magnetic sensor (Hall element, reed relay)+magnet

A plurality of magnetic sensors, such as Hall elements or reed relays, are arranged on the stationary side, while magnets are arranged on the container side at positions opposite some of the Hall elements so that names of medicines are encoded. Whereby, the medicine is identified by binary data output from the magnetic sensors.

(b) Light-emitting element and light-receiving elements+ shut-off plates

A light-emitting element and a plurality of light-receiving elements for sensing light from the light-emitting element are arranged on the stationary side, while shut-off plates for shutting off portions of light rays emitted from the light-emitting element toward the light-receiving elements are arranged on the container side so that names of medicines are encoded. Whereby, the medicine is identified by binary data output from the light-receiving elements.

(c) Microswitches+projections

Plural microswitches are arranged on the stationary side, while projections for turning on microswitches are arranged on the container side at locations opposite some of the microswitches so that names of medicines are encoded. Whereby, the medicine is identified by binary data output from the microswitches.

(d) Bar code reader+bar codes

Bar code readers are provided on the stationary side, while bar codes corresponding to medicine names are arranged on the container side. Whereby, the medicine is identified by reading the bar code by the bar code reader.

(e) Magnetic reading head+magnetic recording media

Magnetic reading heads are provided on the stationary side, while magnetic recording media having magnetic information recorded therein which correspond to names of medicines are provided on the container side. Whereby, the medicines is identified by reading the magnetic information in the magnetic recording media by magnetic reading head.

In the case of items (d) and (e) above, bar codes and magnetic recording media may contain such information as dropping conditions, in addition to names of medicines.

(8) Other Embodiments

Figure 19:
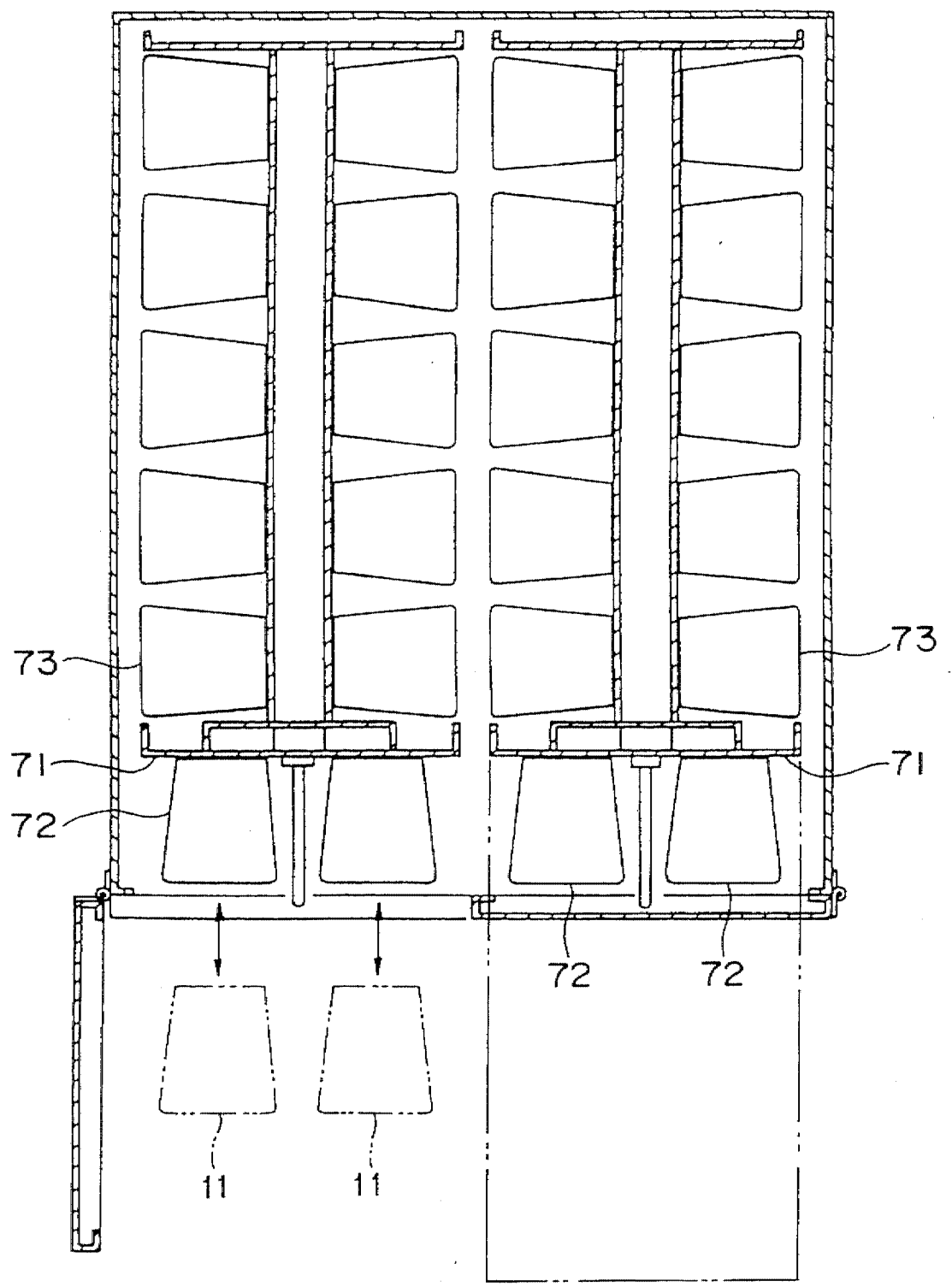
FIG. 19 is a horizontal sectional view of a drawer type tablet feeder.

In the foregoing embodiments, tablet feeders of cylindrical shape (see FIG. 1) are used. It may be noted, however, that they may be of the drawer type. With such a drawer type tablet feeder, it is not possible to draw out a tablet cartridge for change during operation. Therefore, as FIG. 19 shows, it is possible to arrange that supplementary tablet feeders 72 are disposed at the front side of each drawer rack 71 so that a tablet cartridge 11 may be set in any supplementary tablet feeder 72 without involving the trouble of drawing out the rack 71, even when other tablet feeders 73 are in operation. Through this arrangement, even if next tablets are not placed in tablet feeders 73, it is possible to take out a relevant tablet cartridge 11 from the tablet storage shelves 1 and set the same in the supplementary feeder 72 in preparation for a next cycle of packing operation.

Figure 20:
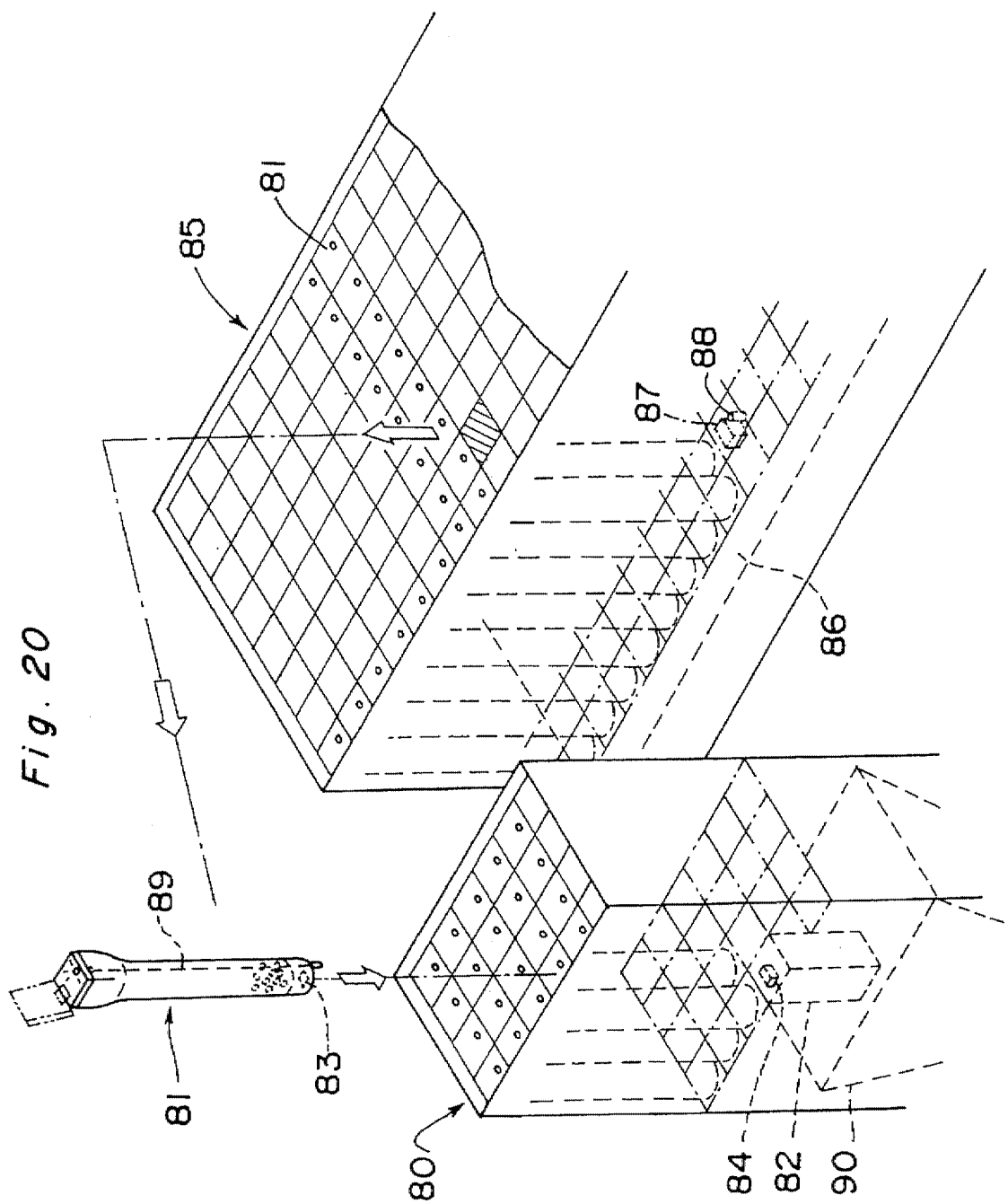
FIG. 20 is a perspective view showing a packing unit designed for use with a cylindrical tablet cartridge, and a storage unit for such tablet cartridges.

The packing apparatus in the foregoing embodiments is of the type adapted for insertion of tablet cartridges from side. However, as FIG. 20 shows, the arrangement is also applicable to a packing apparatus 80 of the type including tablet feeders 82 arranged in a grid pattern which are designed to receive cylindrical tablet cartridges 81 from above. For that purpose, an identification device 83 is provided at the bottom of each tablet cartridge 81 in the same way as in the foregoing embodiments, and a read device 84 is provided in each tablet feeder 82. Further, in order to make the packing apparatus 80 as small as possible, it is desirable to arrange that the number of tablet feeders 82 may be made comparatively small so that only those tablet cartridges 81 which are put in frequent use may be set in position, while a large number of other tablet cartridges 81 may be kept in storage within a store arrangement 85. The store arrangement 85 may have a storage base 86 having a store space divided in a lattice fashion, and at each store location therein are provided a read device 87 for reading an identification device 83 of a tablet cartridge 81, and an indicator lamp 88 for indicating a relevant store location.

In this case, however, the indicator lamp 88 is not visible from outside, if it is disposed at the storage base 86 of the store arrangement 85. Preferably, therefore, optical fibers 89 are arranged in each tablet cartridge 81 stored on the storage base 86, from the bottom up to the top, so that light from indicator lamp 88 may be guided up to the top of the tablet cartridge 81 through the optical fibers 89.

In such a packing apparatus 80 having cylindrical tablet cartridges 81 arranged in a grid pattern, conditions of tablet dropping down to hopper 90 are same with respect to individual tablets, but rolling conditions are different among them. Therefore, it is desirable that this fact be taken into consideration in fixing set locations.

The foregoing embodiments relate to packing apparatuses for medicines in tablet or powder form. However, the present invention is also applicable to a delivery apparatus for medicine bottles, such as ampules, which need not be packed. This delivery apparatus comprises a storage shelves for storing a large number of cartridges in which ampules or the like are housed, and feeders capable of housing a relatively small number of cartridges. Therefore, the apparatus may be of the same arrangement as the above described tablet packing apparatus.

Although the present invention has been fully described by way of the example with reference to the accompany drawing, it is to be noted here that various changes and modifications will be apparent to those skilled in the art. Therefore, unless such changes and modifications otherwise depart from the spirit and scope of the present invention, they should be construed as being include therein.

What is claimed is:

1. A medicine packing apparatus comprising:
    medicine storage shelves for storing a large number of medicine containers each having a medicine contained therein;
    a relatively small number of medicine feed means on each of which one of the medicine containers is set for feeding a medicine in a quantity conforming to a prescription;
    packing means for packing the medicine fed from the medicine feed means by one dose;
    identification means provided for each of the medicine containers;
    read means for reading medicine data from the identification means of the medicine container set on the medicine feed means;
    set location memory means for memorizing the set location for the medicine container on the basis of the medicine data read by the read means; and
    set location search means for searching, on the basis of the set location data for each medicine memorized in the set location memory means, the medicine feed means on which a medicine container for the medicine corresponding to the prescription is set.

2. A medicine packing apparatus comprising:
    medicine storage shelves for storing a large number of medicine containers each having a medicine contained therein;
    a relatively small number of medicine feed means on each of which one of the medicine containers is set for feeding a medicine in a quantity conforming to a prescription;
    medicine distributing means for annularly uniformly distributing the medicine fed from the medicine feed means over a distributing board and then dividing the medicine by one dose to discharge the same;
    packing means for packing the medicine discharged from the medicine distributing means by one dose;
    identification means provided for each of the medicine containers;
    read means for reading medicine data from the identification means of the medicine container set on the medicine feed means;
    set location memory means for memorizing the set location for the medicine container on the basis of the medicine data read by the read means; and
    set location search means for searching, on the basis of the set location data for each medicine memorized in the set location memory means, the medicine feed means on which a medicine container for the medicine corresponding to the prescription is set.

3. A medicine packing apparatus as set forth in claim 1 or 2, further comprising:
    store location memory means for memorizing a store location fixed for each medicine container in the medicine storage shelves;
    store location search means for searching the store location for the medicine corresponding to the prescription on the basis of the store location data memorized in the store location memory means; and
    store location indicator means for indicating the store location for the medicine searched by the store location search means.

4. A medicine packing apparatus as set forth in claim 1 or 2, further comprising:
    read means for reading medicine data from the identification means of the medicine container stored in each store location of the medicine storage shelves;
    store location memory means for memorizing a store location for each medicine container on the basis of medicine data read by the read means;
    store location search means for searching the store location for the medicine corresponding to the prescription on the basis of the store location data memorized in the store location memory means; and
    store location indicator means for indicating the store location for the medicine searched by the store location search means.

5. A medicine packing apparatus as set forth in any one of claims 1 or 2, further comprising:
    proper set location memory means for memorizing a proper set location fixed for each medicine container in the medicine feed means;
    proper location search means for searching the proper set location for the medicine corresponding to the prescription on the basis of the proper location data memorized in the proper set location memory means; and
    proper set location indicator means for indicating the proper set location for the medicine searched by the proper location search means.

6. A medicine packing apparatus as set forth in claim 5, wherein the proper set location memory means memorize the proper set location fixed for each medicine container in such a condition that the medicine which is likely to bounce when dropped is set at a lower location, and that the medicine which is less likely to bounce when dropped is set at a higher location.

7. A medicine packing apparatus as set forth in any one of claims 1 or 2, wherein the packing means performs packing of the medicine corresponding to the prescription at a packing velocity set in consideration of the set location for the medicine and attributes of the medicine including bouncing and rolling characteristics.

8. A medicine packing apparatus as set forth in claim 3, further comprising:
    proper set location memory means for memorizing a proper set location fixed for each medicine container in the medicine feed means;
    proper location search means for searching the proper set location for the medicine corresponding to the prescription on the basis of the proper location data memorized in the proper set location memory means; and
    proper set location indicator means for indicating the proper set location for the medicine searched by the proper location search means.

9. A medicine packing apparatus as set forth in claim 4, further comprising:
    proper set location memory means for memorizing a proper set location fixed for each medicine container in the medicine feed means;
    proper location search means for searching the proper set location for the medicine corresponding to the prescription on the basis of the proper location data memorized in the proper set location memory means; and
    proper set location indicator means for indicating the proper set location for the medicine searched by the proper location search means.

10. A medicine packing apparatus as set forth in claim 8, wherein the proper set location memory means memorize the proper set location fixed for each medicine container in such a condition that the medicine which is likely to bounce when dropped is set at a lower location, and that the medicine which is less likely to bounce when dropped is set at a higher location.

11. A medicine packing apparatus as set forth in claim 9, wherein the proper set location memory means memorize the proper set location fixed for each medicine container in such a condition that the medicine which is likely to bounce when dropped is set at a lower location, and that the medicine which is less likely to bounce when dropped is set at a higher location.

12. A medicine packing apparatus as set forth in claim 3, wherein the packing means performs packing of the medicine corresponding to the prescription at a packing velocity set in consideration of the set location for the medicine and attributes of the medicine including bouncing and rolling characteristics.

13. A medicine packing apparatus as set forth in claim 4, wherein the packing means performs packing of the medicine corresponding to the prescription at a packing velocity set in consideration of the set location for the medicine and attributes of the medicine including bouncing and rolling characteristics.

14. A medicine packing apparatus comprising:

medicine storage shelves for storing a large number of medicine containers each having a medicine contained therein;

a plurality of hoppers for receiving a medicine dispensed according to a prescription data;

medicine distributing means for annularly uniformly distributing the medicine fed from the hoppers on a distributing board and then dividing the medicine by one dose to discharge the same;

packing means for packing the medicine discharged from the medicine distributing means by one dose;

identification means provided for each of the medicine containers;

read means for reading the medicine data from the identification means of the medicine taken out from the medicine storage shelves; and medicine check means for checking the medicine by comparing the medicine data read by the read means with the prescription data.

15. A medicine packing apparatus as set forth in claim 14, further comprising:

store location memory means for memorizing a store location fixed for each medicine container in the medicine storage shelves;

store location search means for searching the store location for the medicine corresponding to the prescription on the basis of the store location data memorized in the store location memory means; and store location indicator means for indicating the store location for the medicine searched by the store location search means.

16. A medicine packing apparatus as set forth in claim 14, further comprising:

read means for reading medicine data from the identification means of the medicine container stored in each store location of the medicine storage shelves;

store location memory means for memorizing a store location for each medicine container on the basis of medicine data read by the read means;

store location search means for searching the store location for the medicine corresponding to the prescription on the basis of the store location data memorized in the store location memory means; and store location indicator means for indicating the store location for the medicine searched by the store location search means.

17. A medicine delivery apparatus comprising:

medicine storage shelves for storing a large number of medicine containers each having a medicine contained therein;

a relatively small number of medicine delivery means on each of which one of the medicine containers is set for delivering a medicine in a quantity conforming to a prescription;

identification means provided for each of the medicine containers;

read means for reading medicine data from the identification means of the medicine container set on the medicine delivery means;

set location memory means for memorizing the set location for the medicine container on the basis of the medicine data read by the read means; and set location search means for searching, on the basis of the set location data for each medicine memorized in the set location memory means, the medicine delivery means on which a medicine container for the medicine corresponding to the prescription is set.

18. A medicine delivery apparatus as set forth in claim 17, further comprising:

store location memory means for memorizing a store location fixed for each medicine container in the medicine storage shelves;

store location search means for searching the store location for the medicine corresponding to the prescription on the basis of the store location data memorized in the store location memory means; and store location indicator means for indicating the store location for the medicine searched by the store location search means.

19. A medicine delivery apparatus as set forth in claim 17, further comprising:

read means for reading medicine data from the identification means of the medicine container stored in each store location of the medicine storage shelves;

store location memory means for memorizing the store location for each medicine container on the basis of medicine data read by the read means;

store location search means for searching the store location for the medicine corresponding to the prescription on the basis of the store location data memorizing in the store location memory means; and store location indicator means for indicating the store location for the medicine searched by the store location search means.

* * * * *